US011013466B2

(12) United States Patent
Lonky

(10) Patent No.: US 11,013,466 B2
(45) Date of Patent: May 25, 2021

(54) DEVICE AND METHOD TO CONTROL AND MANIPULATE A CATHETER

(71) Applicant: HEALOE LLC, Yorba Linda, CA (US)

(72) Inventor: Neal M. Lonky, Yorba Linda, CA (US)

(73) Assignee: HEALOE, LLC, Yorba Linda, CA (US)

(*) Notice: Subject to any disclaimer, the term of this patent is extended or adjusted under 35 U.S.C. 154(b) by 190 days.

(21) Appl. No.: 15/408,321

(22) Filed: Jan. 17, 2017

(65) Prior Publication Data

US 2017/0215798 A1 Aug. 3, 2017

Related U.S. Application Data

(60) Provisional application No. 62/288,377, filed on Jan. 28, 2016.

(51) Int. Cl.
*A61B 5/00* (2006.01)
*A61M 25/06* (2006.01)
(Continued)

(52) U.S. Cl.
CPC ............ *A61B 5/6826* (2013.01); *A61B 5/035* (2013.01); *A61B 5/066* (2013.01); *A61B 5/4356* (2013.01);
(Continued)

(58) Field of Classification Search
CPC ..... A61B 5/6826; A61B 90/50; A61B 5/6852; A61B 5/066; A61B 5/4356; A61B 5/6838;
(Continued)

(56) References Cited

U.S. PATENT DOCUMENTS 1,795,500 A 3/1931 Omundson
2,675,572 A 4/1954 Nomiya
(Continued)

FOREIGN PATENT DOCUMENTS

AT 392411 5/1988
CH 653880 1/1986
(Continued)

OTHER PUBLICATIONS

Idiom. Merriam-Webster.com. Merriam-Wbster, 2020. Retrieved Dec. 2, 2020, from www.merriam-webster.com/dictionary/idiom (Year: 2020).*
(Continued)

*Primary Examiner* — Matthew Kremer
*Assistant Examiner* — Samuel C Kim
(74) *Attorney, Agent, or Firm* — Sci-Law Strategies, PC

(57) ABSTRACT

In various embodiments of the invention, a manipulator attaches to and allows a sheath to be positioned inside the cervix and a catheter to thereby be inserted through the sheath and be positioned in a desired location in the uterus. In various embodiments of the invention, the manipulator may be attached or permanently connected to the sheath. In various embodiments of the invention, the sheath is fenestrated to allow the catheter to be detached from the sheath. In various embodiments of the invention, the manipulator allows the sheath to be positioned through the cervix canal to allow for catheter transmitted intrauterine pressure monitoring or balloon catheter assisted ripening of the cervix.

14 Claims, 9 Drawing Sheets

(51) Int. Cl.

| | |
|---|---|
| *A61B 5/06* | (2006.01) |
| *A61M 25/00* | (2006.01) |
| *A61B 90/50* | (2016.01) |
| *A61M 25/01* | (2006.01) |
| *A61B 90/53* | (2016.01) |
| *A61B 5/03* | (2006.01) |
| *A61B 6/12* | (2006.01) |
| *A61B 17/42* | (2006.01) |
| *A61B 90/00* | (2016.01) |
| *A61M 25/02* | (2006.01) |
| *A61B 17/00* | (2006.01) |

(52) U.S. Cl.
CPC .......... *A61B 5/6838* (2013.01); *A61B 5/6852* (2013.01); *A61B 6/12* (2013.01); *A61B 17/4208* (2013.01); *A61B 17/4241* (2013.01); *A61B 90/50* (2016.02); *A61B 90/53* (2016.02); *A61M 25/0097* (2013.01); *A61M 25/01* (2013.01); *A61M 25/013* (2013.01); *A61M 25/0668* (2013.01); *A61B 5/002* (2013.01); *A61B 5/0011* (2013.01); *A61B 5/0022* (2013.01); *A61B 5/435* (2013.01); *A61B 17/42* (2013.01); *A61B 2017/00438* (2013.01); *A61B 2090/064* (2016.02); *A61B 2503/02* (2013.01); *A61B 2562/12* (2013.01); *A61B 2562/221* (2013.01); *A61M 2025/0188* (2013.01); *A61M 2025/024* (2013.01); *A61M 2025/0213* (2013.01); *A61M 2025/0681* (2013.01); *A61M 2210/1433* (2013.01)

(58) Field of Classification Search
CPC . A61B 5/035; A61B 17/4241; A61B 17/4208; A61B 6/12; A61B 90/53; A61B 17/42; A61B 2090/064; A61B 5/435; A61B 2562/12; A61B 5/002; A61B 2503/02; A61B 2562/221; A61B 2017/00438; A61B 5/0011; A61M 25/01; A61M 2025/0266; A61M 2025/024; A61M 2025/0213; A61M 2025/0188; A61M 2210/1433; A61M 2025/0681
See application file for complete search history.

(56) References Cited

U.S. PATENT DOCUMENTS

| | | | |
|---|---|---|---|
| 2,701,559 A | 2/1955 | Cooper | |
| 2,717,437 A | 9/1955 | De Mestral | |
| 2,811,969 A * | 11/1957 | Shubert | A61B 17/4208 401/8 |
| 2,839,049 A | 6/1958 | Maclean | |
| 2,847,005 A | 8/1958 | Bourne | |
| 2,955,591 A | 10/1960 | Maclean | |
| 3,018,498 A | 1/1962 | Wasserman | |
| 3,263,681 A | 8/1966 | Nechtow | |
| 3,511,242 A | 5/1970 | Agnone | |
| 3,521,332 A * | 7/1970 | Kramer | F16B 2/22 403/188 |
| 3,554,185 A | 1/1971 | Kohl | |
| 3,559,226 A | 2/1971 | Burns | |
| 3,628,522 A | 12/1971 | Kato | |
| 3,774,590 A | 11/1973 | McDonald | |
| 3,777,743 A | 12/1973 | Binard | |
| RE27,915 E | 2/1974 | Kohl | |
| 3,796,211 A | 3/1974 | Kohl | |
| 3,877,464 A | 4/1975 | Vermes | |
| 3,945,372 A | 3/1976 | Milan | |
| 3,995,629 A * | 12/1976 | Patel | A61B 17/42 604/117 |
| 4,016,865 A | 4/1977 | Fredericks | |
| 4,061,146 A | 12/1977 | Baehr | |
| 4,127,113 A | 11/1978 | Nollan | |
| 4,168,698 A | 9/1979 | Ostergard | |
| 4,227,537 A | 10/1980 | Suciu | |
| 4,245,653 A | 1/1981 | Weaver | |
| 4,384,587 A | 5/1983 | Milgrom | |
| 4,396,022 A | 8/1983 | Marx | |
| 4,430,076 A | 2/1984 | Harris | |
| 4,465,072 A | 8/1984 | Taheri | |
| 4,467,816 A | 8/1984 | Schluter | |
| 4,620,548 A | 11/1986 | Hasselbrack | |
| 4,641,662 A | 2/1987 | Jaicks | |
| D289,926 S | 5/1987 | Lonky | |
| 4,700,713 A | 10/1987 | Kist | |
| 4,754,764 A | 7/1988 | Bayne | |
| 4,757,826 A | 7/1988 | Abdulhay | |
| 4,759,376 A | 7/1988 | Stormby | |
| 4,762,133 A | 8/1988 | Bayne | |
| 4,763,669 A | 8/1988 | Jaeger | |
| 4,777,947 A | 10/1988 | Zwick | |
| 4,781,202 A | 11/1988 | Janese | |
| 4,872,243 A | 10/1989 | Fischer | |
| 4,873,992 A | 10/1989 | Bayne | |
| 4,892,831 A | 1/1990 | Wong | |
| 4,932,857 A | 6/1990 | Nishino | |
| 4,946,389 A | 8/1990 | Weissenberger | |
| 4,951,684 A | 8/1990 | McMillan | |
| 4,961,430 A | 10/1990 | Sheahon | |
| 4,965,725 A | 10/1990 | Rutenberg | |
| 4,966,161 A * | 10/1990 | Wallace | A61B 5/035 600/561 |
| 5,022,408 A | 6/1991 | Mohajer | |
| 5,067,195 A | 11/1991 | Sussman | |
| 5,069,224 A | 12/1991 | Zinnanti, Jr. | |
| 5,092,345 A | 3/1992 | Sakita | |
| 5,133,361 A | 7/1992 | Cox | |
| 5,154,694 A | 10/1992 | Kelman | |
| 5,184,626 A | 2/1993 | Hicken | |
| 5,191,899 A | 3/1993 | Strickland | |
| 5,195,964 A * | 3/1993 | Kletzky | A61B 17/42 604/264 |
| 5,197,949 A | 3/1993 | Angsupanich | |
| 5,250,061 A | 10/1993 | Michelson | |
| 5,253,652 A | 10/1993 | Fast | |
| 5,257,182 A | 10/1993 | Luck | |
| 5,259,391 A | 11/1993 | Altshuler | |
| 5,287,272 A | 2/1994 | Rutenberg | |
| 5,315,740 A | 5/1994 | Provost | |
| 5,329,938 A | 7/1994 | Lonky | |
| 5,370,128 A | 12/1994 | Wainwright | |
| 5,421,346 A | 6/1995 | Sanyal | |
| 5,445,164 A | 8/1995 | Worthen | |
| 5,456,265 A | 10/1995 | Yim | |
| 5,462,063 A | 10/1995 | Kist | |
| 5,464,409 A | 11/1995 | Mohajer | |
| 5,470,308 A | 11/1995 | Edwards | |
| 5,476,104 A | 12/1995 | Sheahon | |
| 5,535,756 A | 7/1996 | Parasher | |
| 5,544,650 A | 8/1996 | Boon | |
| 5,549,563 A | 8/1996 | Kroner | |
| 5,623,941 A | 4/1997 | Hedberg | |
| 5,643,307 A | 7/1997 | Turkel | |
| 5,649,943 A | 7/1997 | Amoils | |
| 5,713,369 A | 2/1998 | Tao | |
| 5,722,423 A | 3/1998 | Lind | |
| 5,738,109 A | 4/1998 | Parasher | |
| 5,761,760 A | 6/1998 | Dumler | |
| 5,785,785 A | 7/1998 | Chesley | |
| 5,792,160 A | 8/1998 | Weiss | |
| 5,800,362 A | 9/1998 | Kobren | |
| 5,807,282 A | 9/1998 | Fowler | |
| 5,857,982 A | 1/1999 | Milliman | |
| 5,865,765 A | 2/1999 | Mohajer | |
| 5,868,509 A * | 2/1999 | Crutcher | B43K 23/012 401/7 |
| 5,868,668 A | 2/1999 | Weiss | |
| 5,899,850 A | 5/1999 | Ouchi | |
| 5,913,857 A | 6/1999 | Ritchart | |
| 5,916,228 A | 6/1999 | Ripich | |
| 5,937,870 A | 8/1999 | Gueret | |

(56) References Cited

U.S. PATENT DOCUMENTS

| | | | |
|---|---|---|---|
| 5,951,550 A | 9/1999 | Shirley | |
| 6,053,877 A | 4/2000 | Banik | |
| 6,110,130 A * | 8/2000 | Kramer | A61B 5/1071 600/587 |
| 6,132,421 A | 10/2000 | Clapham | |
| 6,193,674 B1 | 2/2001 | Zwart | |
| 6,258,044 B1 | 7/2001 | Lonky | |
| 6,297,044 B1 | 10/2001 | Eisen | |
| 6,336,905 B1 | 1/2002 | Colaianni | |
| 6,346,086 B1 | 2/2002 | Maksem | |
| 6,376,905 B2 | 4/2002 | Hisano | |
| 6,379,315 B1 | 4/2002 | Claren | |
| 6,387,058 B1 | 5/2002 | Wallach | |
| 6,394,966 B1 | 5/2002 | Gill | |
| 6,408,492 B1 * | 6/2002 | Sparks | A01K 97/08 24/10 R |
| 6,494,845 B2 | 12/2002 | Rutenberg | |
| 6,595,947 B1 | 7/2003 | Mikszta | |
| 6,676,609 B1 | 1/2004 | Rutenberg | |
| 6,730,085 B2 | 5/2004 | George | |
| 6,740,049 B2 | 5/2004 | Wallach | |
| 6,790,654 B2 | 9/2004 | Malinge | |
| 6,860,738 B2 | 3/2005 | Bachmann | |
| 7,004,913 B1 | 2/2006 | Rutenberg | |
| 7,137,956 B2 | 11/2006 | Nishtalas | |
| 7,156,814 B1 | 1/2007 | Williamson, IV | |
| 7,157,233 B1 | 1/2007 | Fischer | |
| 7,413,551 B2 | 8/2008 | Decker | |
| D605,407 S | 12/2009 | Wagner | |
| 7,749,173 B2 | 7/2010 | Larkin | |
| 7,836,539 B2 | 11/2010 | Moskovich | |
| 7,871,574 B2 | 1/2011 | Peltier | |
| 8,152,739 B1 | 4/2012 | McCully | |
| 8,348,856 B1 | 1/2013 | Malanowska | |
| 8,439,847 B2 | 5/2013 | Larkin | |
| 8,517,956 B1 | 8/2013 | Malanowska | |
| 8,617,183 B2 | 12/2013 | Schneider | |
| 8,652,067 B2 | 2/2014 | Lonky | |
| 8,795,197 B2 | 8/2014 | Lonky | |
| 9,028,484 B2 * | 5/2015 | Craig | A61B 42/10 606/41 |
| 9,044,213 B1 | 6/2015 | Lonky | |
| 9,282,950 B2 | 3/2016 | Klein | |
| 9,282,951 B2 | 3/2016 | Lonky | |
| 9,302,078 B2 * | 4/2016 | Lieberman | A61M 25/0668 |
| 9,393,394 B2 | 7/2016 | Lonky | |
| 9,421,346 B2 * | 8/2016 | Callahan | A61M 25/0668 |
| 9,687,642 B2 | 6/2017 | Lonky | |
| 9,895,140 B1 | 2/2018 | Lonky | |
| 10,201,332 B1 | 2/2019 | Lonky | |
| 2001/0022063 A1 | 9/2001 | Korteweg | |
| 2002/0068881 A1 | 6/2002 | Kobren | |
| 2003/0109804 A1 | 6/2003 | Auerbach | |
| 2004/0029658 A1 | 2/2004 | Howe | |
| 2004/0116827 A1 | 6/2004 | Tiberio | |
| 2004/0120989 A1 | 6/2004 | Vadas | |
| 2004/0138642 A1 | 7/2004 | Fischer | |
| 2004/0181170 A1 | 9/2004 | Wallach | |
| 2004/0181185 A1 | 9/2004 | Lee | |
| 2004/0220478 A1 | 11/2004 | Wallace | |
| 2004/0236247 A1 | 11/2004 | Rizvi | |
| 2004/0260199 A1 | 12/2004 | Hardia | |
| 2004/0260201 A1 | 12/2004 | Mueller | |
| 2004/0267191 A1 | 12/2004 | Gifford | |
| 2005/0059905 A1 | 3/2005 | Boock | |
| 2005/0074269 A1 * | 4/2005 | Asselin | B43K 23/06 401/131 |
| 2005/0085845 A1 * | 4/2005 | Hilaire | A61F 2/954 606/194 |
| 2005/0215920 A1 | 9/2005 | Isa | |
| 2005/0251093 A1 * | 11/2005 | Abou-Kansoul | A61M 1/008 604/119 |
| 2006/0052805 A1 | 3/2006 | Cwik | |
| 2006/0200043 A1 | 9/2006 | Jannetty | |
| 2007/0093727 A1 | 4/2007 | Feuer | |
| 2007/0100335 A1 | 5/2007 | Fischer | |
| 2007/0107155 A1 | 5/2007 | Kacher | |
| 2007/0118947 A1 | 5/2007 | Lorenzo | |
| 2007/0161042 A1 | 7/2007 | Zuk | |
| 2007/0282223 A1 | 12/2007 | Larkin | |
| 2008/0188769 A1 | 8/2008 | Lu | |
| 2008/0216763 A1 * | 9/2008 | Ebert | A01K 15/024 119/706 |
| 2009/0012424 A1 | 1/2009 | Huschmand | |
| 2009/0024155 A1 * | 1/2009 | Lee-Sepsick | A61B 17/12099 606/191 |
| 2009/0112239 A1 | 4/2009 | To | |
| 2009/0149860 A1 | 6/2009 | Scribner | |
| 2009/0326414 A1 | 12/2009 | Peltier | |
| 2010/0011483 A1 * | 1/2010 | Pinkart | A63B 53/14 2/161.3 |
| 2010/0210968 A1 | 8/2010 | Lonky | |
| 2010/0249649 A1 | 9/2010 | Larkin | |
| 2011/0152881 A1 * | 6/2011 | Conner | A61B 34/30 606/130 |
| 2011/0172557 A1 | 7/2011 | Lonky | |
| 2011/0268610 A1 | 11/2011 | Recknor | |
| 2013/0267870 A1 | 10/2013 | Lonky | |
| 2014/0128773 A1 | 5/2014 | Lonky | |
| 2014/0358158 A1 | 12/2014 | Einarsson | |
| 2016/0015259 A1 * | 1/2016 | Mody | A61B 8/12 600/439 |
| 2016/0100862 A1 | 4/2016 | Parys | |
| 2017/0021151 A1 | 1/2017 | Lonky | |
| 2017/0112477 A1 | 4/2017 | Benning | |
| 2018/0035983 A1 | 2/2018 | Lonky | |
| 2018/0296800 A1 | 10/2018 | Kato et al. | |

FOREIGN PATENT DOCUMENTS

| | | | |
|---|---|---|---|
| EP | 2166965 | 7/2008 | |
| WO | WO2005084555 | 9/2005 | |
| WO | WO 2007101994 | 9/2007 | |
| WO | WO 2007101994 A1 * | 9/2007 | A61B 17/4241 |
| WO | WO2009012392 | 1/2009 | |
| WO | WO2012125757 | 9/2012 | |
| WO | WO 2015134568 | 9/2015 | |

OTHER PUBLICATIONS

Blute, Renal brush biopsy: Survey of indications, techniques and results, J Urol., Aug. 1981, vol. 126(2), pp. 146-149.

Boon et al., "Confocal Sectioning of Thick, Otherwise Undiagnosable Cell Groupings in Cervical Smears" Acta Cytol., vol. 37, pp. 40-48 (1991).

Boon et al., "Exploiting the "Toothpick Effect" of the Cytobrush by Plastic Embedding of Cervical Samples" Acta Cytol., vol. 35, pp. 57-63 (1991).

Boon, "A model for quantitative follow-up studies of cervical lesions," Diagn Cytopathol., 1992, vol. 8(1), pp. 8-17.

Butler, B., "Kuper brush in the diagnosis of endometrial lesions," The Lancet, Dec. 1971, vol. 298(7739), pp. 1390-1392.

DeGirolami, "Histo-brush technic for endometerial tissue study," Obstet Gynecol., Dec. 1961, vol. 28(6), pp. 861-866.

Dowlatshahi et al., "Evaluation of brush cytology as an independent technique for detection of esophageal carcinoma" J Thoracic and Cardiovascular Surgery, vol. 89, No. 6, pp. 848-851, Jun. 1985.

Fennessy, "Transbronchial biopsy of peripheral lung lesions," Radiology, May 1967, vol. 88(5), pp. 878-882.

Firestone, "Needle lung biopsy, bronchial brushing and mediastinoscopy in Management of Chest Diseases," Calif Med., Sep. 1973, vol. 119(3), pp. 1-5.

Gahres et al., "Histo-brush technic for Endometrial Tissue Study", Obstet Gynecol vol. 28, pp. 861-866 (1966)—Front Page Only.

Goldstein, "Esophageal biopsy utilizing a flexible brush," Gastrointest Endosc., Aug. 1968, vol. 15(1), pp. 53-55.

Granqvist, "Colonoscopic biopsies and cytological exam in chronic ulcerative colitis," J Gastroenterology, Apr. 1980, vol. 15(3), pp. 283-288.

(56) References Cited

OTHER PUBLICATIONS

Hardwick, "Brush biopsy in the diagnosia of neoplasia in Bartlett's esophagus," Disease Esophagus, Oct. 1997, vol. 10(4), pp. 233-237.
Iaccarino, "Percutaneous intralesional brushing of cystic lesions of bone: a technical improvement of diagnostic cytology," Skeletal Radiol, 1990, vol. 19(3), pp. 187-90.
International Search Report of PCT/US2008/70341 published as WO2009012392 dated Oct. 22, 2008.
Johnsson, "Cytological brush techniques in malignant disease of the endometrium," Acta Obstet Gynecol Scand, Jan. 1968, vol. 47, issue 1, pp. 38-51.
Johnsson, "Cytological diagnosis of endometrial disorders with a brush technique," Acta Obstet Gynecol Scand., 1971, vol. 50(2), pp. 141-148.
Kovnat, "Bronchial brushing through the flexible fiberoptic bronchoscope in the diagnosis of peripheral pulmonary lesions," Chest, Feb. 1975, vol. 67(2), pp. 179-184.
Liu, "Transcervical chorionic villus biopsy with a brush," Prenat Diagn., Sep.-Oct. 1985, vol. 5(5), pp. 349-355.
Maksem, "Endometrial brush cytology of advanced postmenopausal endometrium . . . ," Diagn Cytopathol., Nov. 1998, vol. 19(5), pp. 338-343.
Matsuda, "Bronchial brushing and bronchial biopsy: comparison of diagnostic accuracy and cell typing reliability in lung cancer," Thorax, Jun. 1986, vol. 41(6), pp. 475-479.
Meulman, "Predictions of various grades of cervical neoplasia on plastic-embedded cytobrush samples," Anal Quant Cytol Histol., Feb. 1992, vol. 14(1), pp. 60-72.
Mills, "Transcatheter brush biopsy of intravenous tumor thrombi," Radiology, Jun. 1978, vol. 127(3), pp. 667-670.
Morteza, "Brush and forceps biopsy of billary ducts via percutaneous transhepatic catheterization," Radiology, Jun. 1980, vol. 135, pp. 777-778.
Moskowitz, "To brush or not to brush is there really a question?," Chest, Jun. 1971, vol. 59(6), pp. 648-650.
Mullins, "A new technique for transbronchial biopsy in infants and small children," Pediatr Pulmonol, Oct. 1995, vol. 20(4), pp. 253-257.
Payne, "Diagnostic accuracy of cytology and biopsy in primary bronchial carcinoma," Thorax, Jun. 1979, vol. 43(3), pp. 294-299.
Pipkorn, "A brush to harvest cells from the nasal mucosa for microscopic and biochemical analysis," J Immunol Methods, Aug. 9, 1988, vol. 112(1), pp. 37-42.
Portner, "New devices for biliary drainage and biopsy," Radiology, Jun. 1982, vol. 138, pp. 1191-1195.
Raney, "Detection of carcinoma of upper urinary tract with steerable brush biopsy," Urology, Jul. 1979, vol. 14(1), pp. 77-78.
Ravinsky, "Cytologic features of primary adenoid cystic carcinoma of the uterine cervix. A case report," Acta Cytol., Nov.-Dec. 1996, vol. 40(6), pp. 1304-1308.
Riise et al., "Bronchial brush biopsies for studies of epithelial inflammation in stable asthma and nonobstructive chronic bronchitis" Eur Respir J vol. 9, pp. 1665-1671 (1996).
Riise, "A bronchoscopic brush biopsy study of large airway mucosal pathology in smokers . . . ," Eur Respir J., Apr. 1992, vol. 5(4), pp. 382-386.
Roth et al., "Cytologic Detection of Esophageal Squamous Cell . . . " Cancer, vol. 80, No. 11, Dec. 1, 1997.
Sanderson, "Use of a new controllable-tip brush with the flexible fiber bronchoscope," Chest, Jun. 1974, vol. 65(6), pp. 620-621.
Sheline, "Fluoroscopically guided retrograde brush biopsy in the diagnosis of transitional cell carcinoma of the upper urinary tract . . . ," Am J Roentgenology, Sep. 1989, vol. 153(2), pp. 313-316.
Willson, "Bronchial brush biopsy with a controllable brush," Am J Roentgenology, Jul. 1970, vol. 109(3), pp. 471-477.
Zavala, "Use of Bronchofiberscope for bronchial brush biopsy: diagnostic results and comparison with other brushing techniques," Chest, Jun. 1973, vol. 63(6), pp. 889-892.
Zeppa, "A model for quantitative follow-up studies of cervical lesions," Diagn Cytopathol, 1992, vol. 8(1), pp. 8-17.
International Search Report, PCT/US2008/070341, dated Oct. 22, 2008.
Extended European Search Report, PCT/US2008/070341, dated May 11, 2012, 7 pages.
Australian Patent Exam Report 20130806, dated Aug. 6, 2013, 5 pages.
European Office Action, 08796246.0-1654, dated Jun. 5, 2015, 5 pages.
Article 94(3) European Communication, Application No. 08796246.0 PCT/US2008/070341, dated Jul. 4, 2016, 4 pages.
ISR of Application No. 08796246, PCT/US2008/70341 published as WO2009012392 dated Oct. 22, 2008, 6 pages.
Extended ESR of Application No. 08796246, PCT/US2008/070341, May 11, 2012, 6 pages.
Communication under Article 94 of Application No. 08796246, PCT/US2008/070341, dated Jun. 8, 2015, 5 pages.
International Search Report, PCT/US2017/014190, dated Apr. 10, 2017, 13 pages.
International Preliminary Report on Patentability of PCT/US17/14190, published as WO2017/132051, dated Jul. 31, 2018, 7 pages.
Extended ESR of Application No. 17744713.3, PCT/US2017/014190, Aug. 19, 2019, 7 pages.

* cited by examiner

DEVICE AND METHOD TO CONTROL AND MANIPULATE A CATHETER

PRIORITY CLAIM

This application claims priority to U.S. provisional application No. 62/288,377, filed Jan. 28, 2016, inventor Neal M. Lonky entitled "DEVICE AND METHOD TO CONTROL AND MANIPULATE A CATHETER", which is expressly incorporated by reference in its entirety.

FIELD OF THE INVENTION

This invention relates to a device and method of inserting, orienting, and guiding the placement and angle of trajectory of a catheter in the uterus.

BACKGROUND OF THE INVENTION

During pregnancy, external tocodynamometers can be used to measure tension across the abdominal wall and detect contraction frequency and duration. However, the appearance of contractions by external monitoring can be affected not only by contraction strength but also by maternal habitus, position, gestational age, and monitor location on the abdomen.

An intrauterine pressure catheter (IUPC) is a device which can be placed into the amniotic space during labor in order to directly measure the strength of uterine contractions. IUPC's work by measuring pressure within the amniotic space using a pressure transducer at the tip of the catheter. The pressure transducer allows for more accurate quantification of contraction strength. The pressure transducer can be used to assess (using Montevideo units (MVUs)) the status of the labor.

Using an IUPC is recommended in cases of suspected labor dystocia or during induction. MVUs are calculated by subtracting the baseline uterine pressure from the peak uterine pressure of each contraction in a 10-minute window of time and then taking the sum of these pressures. Two hundred Montevideo units (200 MVU) or more is considered adequate for normal labor progression.

Labor dystocia is defined as difficult labor or abnormally slow progress of labor. Induction is a procedure used to stimulate uterine contractions during pregnancy before labor begins on its own. Successful labor induction leads to a vaginal birth. A health care provider might recommend labor induction for various reasons, primarily when there's concern for a mother's health or a baby's health. Each labor process is individualized, and relies upon well-studied, wel-informed decision making instituting reliable mechanisms to ensure a safe birth. Most induction methods require monitoring of uterine and fetal activity, as well as other considerations such as oral intake and activity of the mother. There are a variety of ways in which induction can be accomplished. If the cervix is firm, long, or closed, cervical ripening can be recommended before initiating labor. Induction sometimes necessitates a cervical ripening phase, which is advisable if the cervix is not 2-3 cm open, and more than 80% effaced and results in an increased likelihood for a successful induction and vaginal delivery. If the pregnancy is beyond 38 weeks and the cervix is sufficiently open, a medical examiner can sweep or strip the cervical membrane thereby pressing the amniotic sac off the cervix without piercing the amniotic sac. When effective, this procedure can stimulate the release of oxytocin from the pituitary gland helping to initiate contractions within 48 hours.

Conventional insertion of the IUPC through an introducer sheath nestled between two fingers requires a cervical dilation sufficient to fit the two finger tips, and the gulley between the fingers to stabilize the trajectory and guide the accuracy of insertion through the cervix and around the fetal presenting part (see FIG. 1).

Foley catheter balloons can be used to mechanically dilate the cervix and have been helpful to ready the cervix for induction. With this method, a small piece of rubber tubing is placed through the cervix and a balloon inside the tubing is inflated just inside the inner edge of the cervix. The balloon, given time and sometimes in conjunction with small amounts of synthetic oxytocin, stimulates the genesis of prostaglandins and proteases which in concert, gently soften and open the cervix. The balloon may come out on its own, or be removed with gentle traction.

Artificial rupture of membranes, amniotomy or the breaking of the amniotic sac can be used on its own to initiate labor or in conjunction with other mechanisms of ripening and induction. This is usually dependent upon the cervical exam, the firmness of the fetal presenting part on the cervix, and whether or not this is the mother's first baby. While amniotomy can be used at any time after the cervix has dilated, it is often reserved for when the ripening phase has been completed. The process of amniotomy is similar to a slightly longer cervical exam wherein a small hook is used to painlessly put a hole in the water bag which has no nerve endings. During the remainder of the labor, amniotic fluid will leak out intermittently. Some womens' bodies respond quickly to this technique while others require additional measures to induce labor via triggering cervical softening and facilitating dilation during uterine contractions and application of the fetal presenting part to the lower uterine segment and cervix.

Synthetic oxytocin, has been used effectively for labor induction for many years and there is a vast amount of data that supports its safety in obstetric and midwifery practice. This hormone is infused, in a diluted form, intravenously. It may be the first-line medication used for induction, or may be used after a cervical ripening agent has been introduced or following amniotomy.

SUMMARY OF THE INVENTION

In an embodiment of the invention, the introducer sheath can be oriented and positioned in the cervix using a manipulator that contacts a single finger to allow the sheath to be guided through a narrow cervix with room for a single finger. The manipulator is attached to a sheath and is passed through the cervix to allow a catheter to be passed through the sheath and the catheter end positioned appropriately in the uterus. The station of the fetal presenting part or breech as the presenting part in the lower uterine segment abuts against the upper cervix in early labor, preventing advancement of the introducer sheath directly into the uterine amniotic cavity. Thus, the placement of the introducer is limited to the upper cervical-presenting part junction where the catheter can be pushed forward sliding inside the sheath an angled around the presenting part into the uterine cavity. The introducer sheath can then be retracted from the cervix and separated from the catheter without disturbing the location of the catheter or the position of the catheter end. In an embodiment of the invention, the sheath has a fenestrated end to allow the catheter to be easily separated from the sheath.

In an embodiment of the invention, the embodiments stabilize the catheter inside the gulley between the two fingers such that the sheath can be oriented and positioned in the cervix using a manipulator that contacts two fingers to allow the sheath to be guided through a narrow cervix with room for two fingers. In another embodiment of the invention, the manipulator stabilizes the catheter when the two finger gulley technique is chosen by the medical examiner.

While existing insertion method occurs during the cervical exam accomplished using two fingers, the embodiments of the invention tether the face of the sheath opposite its fenestration to the ventral aspect of the second or third metacarpal of the index or middle finger. This permits entry of the finger, thus safe guidance of the angle of insertion and trajectory relative to the fetal presenting part at a smaller dilation than can be possible using the traditional two-finger approach. In various embodiments of the invention, a single finger manipulator to the sheath using a clip or Velcro manipulator at the sheath non fenestrated side. The aspect of this connector relative to the finger can employ a double clip design, a clip and strap design, a clip and thimble cup design, or a Velcro to Velcro manipulator design.

The IUPC introducer sheath is usually a stiff sheath of a common length of approximately 25 cm to approximately 40 cm and requires a vaginal hand placement, and the alternate hand to angle the trajectory and stabilize the location of the introducer sheath between the medical examiner's fingers towards and into the cervix. Thus, in clinical practice, introduction of the IUPC into the amniotic cavity is a two-handed procedure with the second non vaginally placed external hand used both for guidance of the introducer sheath into its proper location for catheter placement, but also for pushing or inserting the IUPC through the introducer sheath past the fetal presenting part into the amniotic cavity. The distal end will ensheath the catheter while the proximal end usually is comprised of a flat angled tab used to pull apart and detach the introducer sheath from the catheter following insertion.

In one embodiment of the invention, the various finger manipulator embodiments can be detachable from the catheter by a clip, strap, snap, or Velcro mechanism. In another embodiment, the finger manipulator can be welded or glued to the surface of the introducer sheath opposite the fenestration.

In various embodiments of the invention, the manipulator allows the medical examiner to guide, accurately insert, and manipulate the catheter trajectory by attaching to and aiming the introducer sheath with the manipulator anchoring it to one finger. Thus the cervix need not be sufficiently open as to require a dilation correlating to the diameter of the medical examiner's two fingers.

BRIEF DESCRIPTION OF THE DRAWINGS

The invention is illustrated by way of example and not by way of limitation in the figures of the accompanying drawings in which like references indicate similar elements. This invention is described with respect to specific embodiments thereof. Additional features can be appreciated from the Figures in which.

DETAILED DESCRIPTION OF THE INVENTION

Definitions

Figure 1:
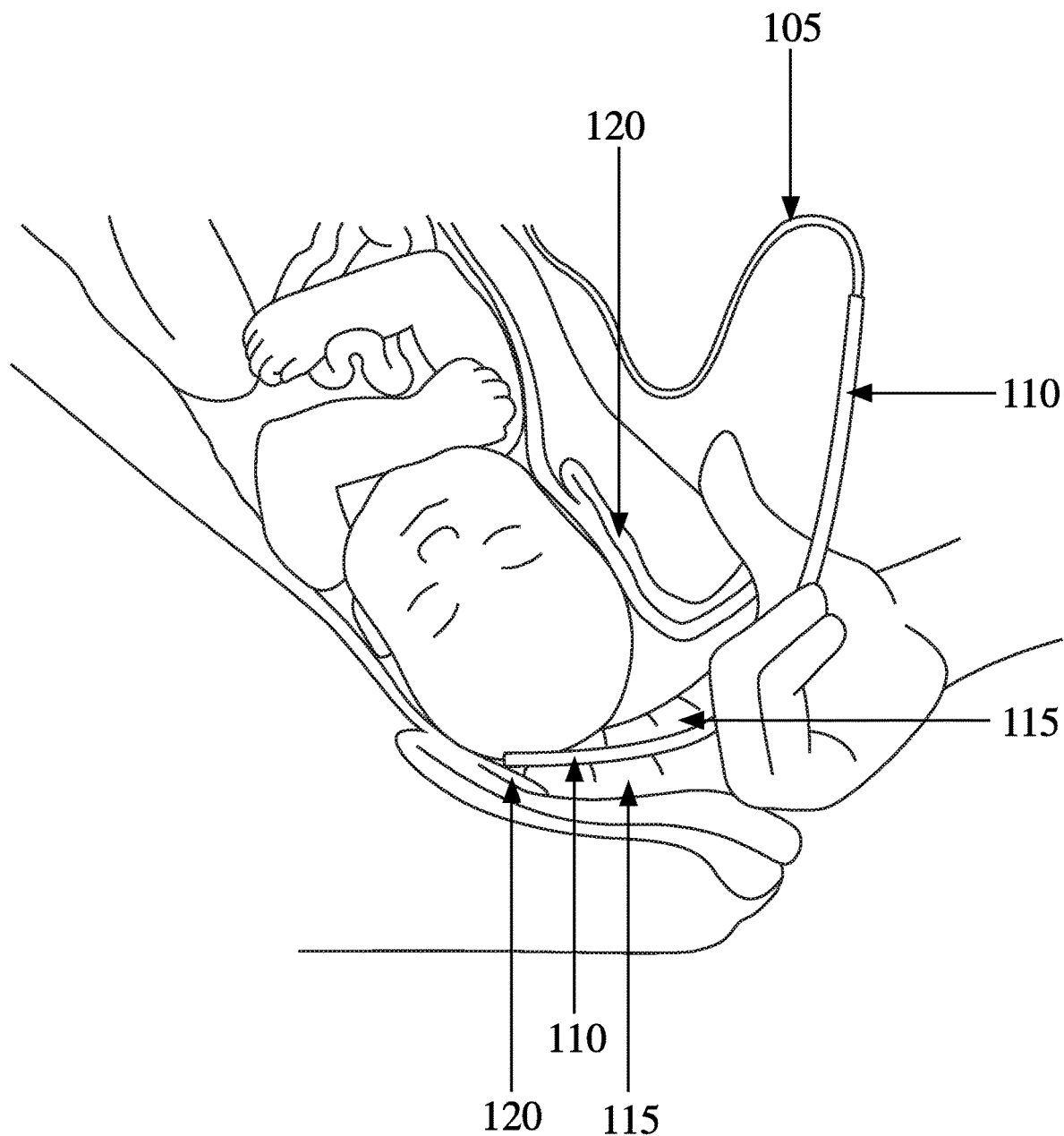
FIG. 1 is a schematic drawing of a fetus within the uterus where a medical professional is using two fingers to pass a catheter through the cervix, as described in the prior art.

The transitional term "comprising" is synonymous with "including," "containing," or "characterized by," is inclusive or open-ended and does not exclude additional, unrecited elements or method steps.

The transitional phrase "consisting of" excludes any element, step, or ingredient not specified in the claim, but does not exclude additional components or steps that are unrelated to the invention such as impurities ordinarily associated with a composition.

The transitional phrase "consisting essentially of" limits the scope of a claim to the specified materials or steps and those that do not materially affect the basic and novel characteristic(s) of the claimed invention.

The surgical guide or hollow tube can be made from one or more materials selected from the group consisting of metal coated glass tube, metal coated fused silica tube, machinable glass, metal coated machinable glass, ceramic, metal coated ceramic, plastic, metal coated plastic and metal. Plastics can be made from one or more polymers selected from the group consisting of high impact polystyrene, polyphenylene ether and polystyrene impregnated with pentane, a blend of polyphenylene ether and polystyrene impregnated with pentane or polyethylene, polypropylene, polypropylene/polypropylene composites, polycarbonate, low density polyethylene, high density polyethylene, acrylonitrile butadiene styrene copolymers, polyphenoxy ether alloyed with high impact polystyrene, polyether, polyglycol, polyester, polyethylene, poly(halogen)ethylene, polypropylene, polyvinylidene halogen, polymethylmethacrylate, polyacrylonide, polycaprolactone, polylactide, poly butylene succinate, polybutylene succinate adipate, polybutylene succinate terephthalate, poly-hydroxypropionate, poly-hydroxybutyrate, poly-hydroxyvalerate, poly-hydroxyhexanoate, poly-3-hydroxyoctanoate, poly-3-hydroxyphenylvaleric acid and poly-3-hydroxyphenylhexanoic acid.

The phrase 'radio-opaque material' or 'signal-opaque material' can include metals and a range of thermoplastic compounds for injection-molding whose opacity to X-rays guarantee shielding comparable to that of metals. It is possible to optimize the shielding efficiency and contrast by selecting the type of charge and dosing the concentration of the constituent polymer molecule and fillers used. LoPro Clear™ is a polyurethane that is x-ray visible and optically transparent. LoPro Plus™ is reinforced with nanoparticles for improved strength of thin wall catheters.

A 'fluoroscope' is a device equipped with a fluorescent screen on which the internal structures of an optically opaque object, such as the human body, may be continuously viewed as shadowy images formed by the differential transmission of x-rays through the object.

The word 'catheter' means a thin flexible tube of less than $1 \times 10^{-2}$ meters external radius made from medical grade materials that can be inserted through the cervix into the uterus to perform a surgical procedure.

The phrase 'presenting part' includes fetal head, fetal torso or breech.

The phrase 'remains in position' means the catheter does not move more measurably from the desired position. In an embodiment of the invention, the catheter does not move more than approximately 2 cm from the desired position as the sheath is removed from the vagina. In an embodiment of the invention, the catheter does not move more than approximately 5 cm from the desired position as the sheath is removed from the vagina. In this range, approximately means plus or minus twenty (20) percent.

The words 'sheath' or 'introducer sheath' means a stiff hollow tube that allows trans-vaginal entrance towards the junction of the fetal presenting part and the cervix. It can be fenestrated or non fenestrated and can serve as a sheath for the inner catheters that can be advanced with the ideal catheter placement location being the inner cervix or the amniotic space. The sheath can be a slightly larger internal radius than the catheter external radius that can be inserted through the cervix adjacent to the fetal presenting part angled toward the uterus to allow the catheter to be inserted into the uterus. The words 'fenestrated sheath' or 'fenestrated introducer sheath' mean a sheath with an opening to allow easy removal of the fenestrated sheath from the catheter.

The word "manipulator" means a device to attach a finger or fingers to the sheath or catheter to stabilize, control, direct, advance or withdraw such sheath or catheter to or from the cervix, cervical canal, or the space between the cervix and fetal presenting part. The manipulator can be made of one or more materials selected from the group consisting of plastic, metal, organic flexible material, synthetic flexible material and/or Velcro. In an embodiment of the invention, the manipulator can be rigid. In an alternative embodiment of the invention, the manipulator can be flexible. In an embodiment of the invention, the manipulator can be adjustably fixed to the sheath. In an alternative embodiment of the invention, the manipulator can be detachable from the sheath. In another alternative embodiment of the invention, the manipulator can be permanently secured to the sheath. The manipulator converts the medical professional's finger into an applicator to control, apply and position the catheter.

The word 'associated' with reference to the finger or gloved finger with the manipulator means the finger and/or gloved finger can be inserted into the manipulator, the finger and/or gloved finger can be attached to the manipulator, the finger and/or gloved finger can be detachably attached to the manipulator, the finger and/or gloved finger can be affixed into the manipulator or the finger and/or gloved finger can be detachably affixed into the manipulator. The word 'positioning' can refer to positioning the catheter or positioning the sheath. When positioning the catheter the medical examiner can insert or withdraw the catheter inside the sheath to position the catheter inside the cervix and uterus. When positioning the sheath with the manipulator, the medical examiner can use the manipulator to adjust the proximal end of the sheath to position the catheter inside the cervix and uterus. The manipulator can be used to rock the sheath and change the angle of trajectory of the catheter relative to the fetal head and the cervical canal to gradually introduce the catheter so that it enters the amniotic space safely. By using one hand to position the catheter and the other hand to position the sheath, the medical examiner can correctly position the catheter inside the cervix and uterus. Advancing cervical dilation with balloon catheters can be used to introduce a catheter in one or both the upper cervical space and the lower uterine space which can also be accomplished with the manipulator adjusting the sheath.

A 'single finger manipulator' is a device that allows the sheath to be manipulated using at most one finger and the thumb. For clarity a device that requires two (2) or more fingers to introduce the sheath into the cervix or manipulate the sheath through the cervix into the uterus is not a single finger manipulator.

The word 'cervix' means the lower part of the uterus in the human female reproductive system. In a non-pregnant woman, the cervix is usually between approximately 2 and approximately 3 cm long and roughly cylindrical in shape. The narrow, central cervical canal runs along its entire length, connecting the uterine cavity and the lumen of the vagina. The opening into the uterus is called the internal os and the opening into the vagina is called the external os. The lower part of the cervix, known as the vaginal portion of the cervix (or ectocervix), bulges into the apex of the vagina.

The word 'uterus' means the womb and extends from the cervix (which opens into the vagina) to the uterine corpus and fallopian or uterine tubes. The uterus includes the central cervical canal (uterine cervix).

The word 'antepartum' means of or noting the period prior to childbirth; before delivery. The word 'intra-partum' means where the patient is in labor and undelivered.

The phrase 'steer the sheath' means position and orient the sheath in the cervix with or without the aid of fluoroscopy.

The phrase 'release and adjust to the sheath' means detach, position and reattach along the length of and relative to the sheath.

The word 'connected' means 'inserted', 'attached', fixed' or otherwise associated to be able to use a finger in the manipulator to manipulate the sheath in the cervix to steer or orient the catheter correctly in the uterus.

In addition to IUPC and Foley catheters, other uterine balloons include Bakri balloon, BT-cath balloon tamponade catheter, Rusch balloon, condom catheters, the Sengstaken-Blakemore tube and cervical ripening catheters which employ a double balloon design.

In the following description, various aspects of the present invention will be described. However, it will be apparent to those skilled in the art that the present invention may be practiced with only some or all aspects of the present invention. For purposes of explanation, specific numbers, materials, and configurations are set forth in order to provide a thorough understanding of the present invention. However, it will be apparent to one skilled in the art that the present invention may be practiced without the specific details. In other instances, well-known features are omitted or simplified in order not to obscure the present invention.

Various operations will be described as multiple discrete steps in turn, in a manner that is most helpful in understanding the present invention; however, the order of description should not be construed as to imply that these operations are necessarily order dependent.

Various embodiments will be illustrated in terms of exemplary classes and/or objects in an object-oriented programming paradigm. It will be apparent to one skilled in the art that the present invention can be practiced using any number of different classes/objects, not merely those included here for illustrative purposes. Furthermore, it will also be apparent that the present invention is not limited to any particular software programming language or programming paradigm.

It should be noted that references to 'an' or 'one' embodiment in this disclosure are not necessarily to the same embodiment, and such references mean at least one.

The placement of an IUPC occurs during a digital vaginal examination prior to or during labor when internal catheter monitoring is needed to more accurately measure the intensity and timing of contractions. Currently, the dilemma facing the medical examiner is the requirement of needing a dilation sufficient to permit insertion of two finger so as to make it easier for the medical examiner to direct an IUPC in the uterus. The medical professional inserts two fingers that are insinuated into the opening of the dilated uterine cervix, with the fingertips approaching or contacting the junction between the fetal presenting part and the endocervical canal or lower uterine segment (see FIG. 1). This requires prior cervical ripening and artificial balloon or *Laminaria japonica* dilatation or naturally occurring cervical dilation during labor to a sufficient diameter to permit entry of the fingers. The cervical dilation is measured clinically using two fingers that are spread once inside the cervical canal, with the width between the fingers as the measured approximation of cervical dilation diameter in centimeters. A fully dilated cervix wherein the expulsion of the fetal presenting part is permitted voluntarily or that will allow fetal delivery to occur is approximately ten centimeters. With the average finger diameter, being able to insert two fingers, commonly the index and middle finger, in the dilating cervix commonly is possible at a dilation of two to three centimeters dilation. This is the common dilation at which an IUPC introducer sheath can be placed through the cervix towards the fetal presenting part cervical junction. The introducer sheath is commonly curved with the distal convex portion guided by the medical examiners towards the fetal presenting part, and the concave portion angling and steering the trajectory of the catheter in a direction that can facilitate curvature of the catheter around the fetal presenting part, and not directly into the cervical stroma or fetal presenting part. The final approximately 10 cm to approximately 15 cm curvature of the introducer sheath gives the more flexible internal IUPC catheter elastic memory to induce such curvature when the catheter is advanced into the amniotic cavity around the fetal presenting part.

Figure 12A:
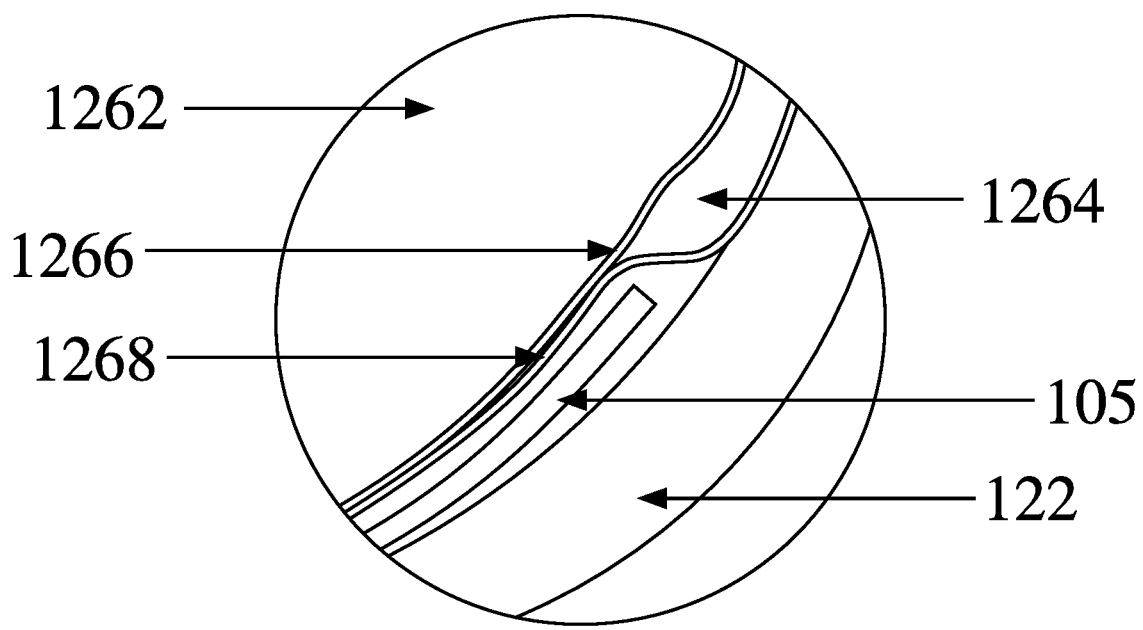
FIG. 12A is a schematic drawing of a catheter that has been incorrectly positioned beneath the amnion and chorion, between the chorion and the endometrial lining.
Figure 12B:
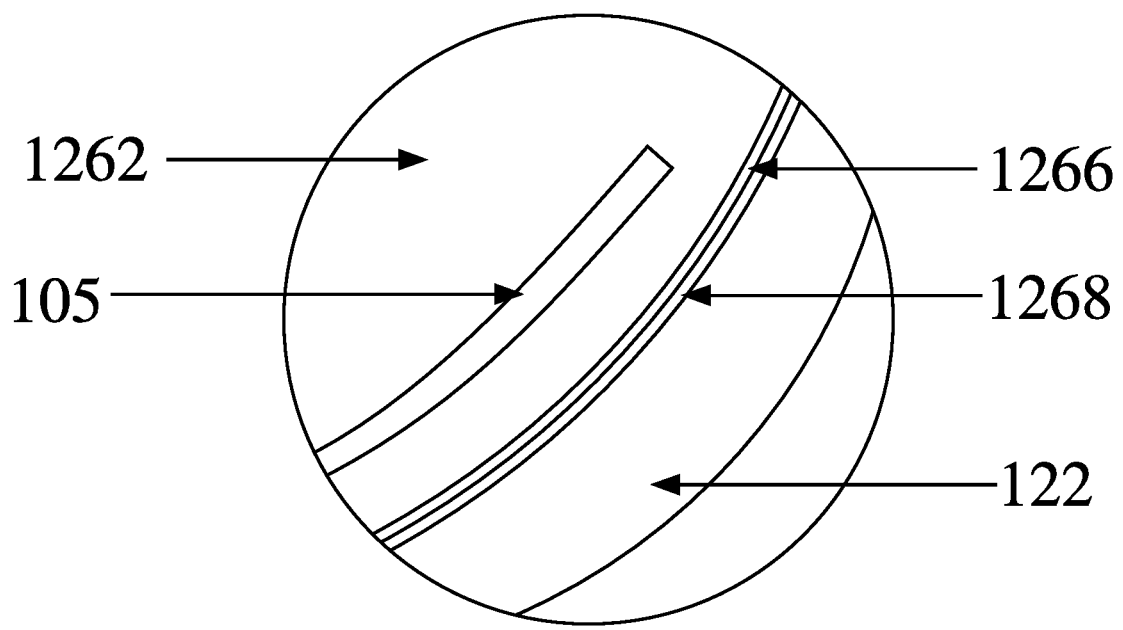
FIG. 12B is a schematic drawing of a catheter that has been correctly positioned in the amniotic fluid space rather than beneath the amnion, according to various embodiments of the invention.

The placement of the IUPC introducer fenestrated sheath used to guide the insertion of the IUPC catheter requires placement between the gulley created between the index and middle finger to stabilize the location of insertion towards the fetal presenting part-cervical junction. Two fingers insinuate into the cervical opening so that a proper placement angle can be accomplished, the trajectory of the catheter is curved around the fetal presenting part into the amniotic cavity. Improper placement can result in misdirection of the catheter angle, and due to its narrow diameter and stiffness, there is a risk that the catheter will be pushed laterally into and through the cervical stroma into the vasculature or nearby structures leading to perforation of the cervix or lower uterine segment, or hemorrhage (see FIG. 12A). FIG. 12A shows a schematic drawing of a catheter 105 that has been incorrectly positioned beneath the amnion 1266 and chorion 1268, i.e., between the chorion 1268 and the endometrial lining 122. If the placenta 1264 is low lying, improper advancement of the catheter 105 can insinuate in an intra-ovular location between the amnion 1266 and chorion 1268, or chorion 1268 and the uterine musculature (between amnion 1266/chorion 1268 (membranes) and the uterine wall defines extra-ovular placement, if the catheter is in the area of the margin of placenta, that can trigger separation of the chorion 1268 from the uterine wall toward the placenta 1264 attachment and trigger a separation defined as abrutio placenta or placental abruption), causing the placenta 1264 to peel away from the uterus into the amniotic fluid space 1262 or the uterus to perforate. Following proper placement into the uterine cavity (see FIG. 12B), the stiffer introducer sheath (not shown) is removed from the vagina and peeled off the IUPC catheter at the fenestration which is wide enough to permit the exit of the catheter 105 from the sheath. FIG. 12B shows a schematic drawing of a catheter 105 that has been correctly positioned in the amniotic fluid space 1262 rather than beneath the amnion 1266, according to various embodiments of the invention.

FIG. 1 shows a schematic drawing of a fetus within the uterus where a medical professional is using two fingers 115 to pass a catheter 105 through a sheath 110 into the cervix between the endometrial lining and the amniotic sac 120, as described in the prior art. While the prior art shows a two finger vaginal exam of woman in labor with a dilated cervix, which is usually more than approximately 2 cm, and sometimes approximately 3 cm, the two finger examination becomes problematic if the medical professional is an adult male with large fingers. In this range approximately refers to plus or minus ten (10) percent. The medical professional is instructed to place the sheath 110 in the gulley between the two fingers. The prior art sheath is removed from the catheter by guidance using the vaginal hand and pulling back of the introducer sheath leading to withdrawal using the opposite hand.

In an embodiment of the invention, the sheath can be the length of the palm without exiting the vaginal opening, allowing for single hand manipulation if already attached to the fingers or finger for stabilization angling of the IUPC at its distal end.

Figure 2:
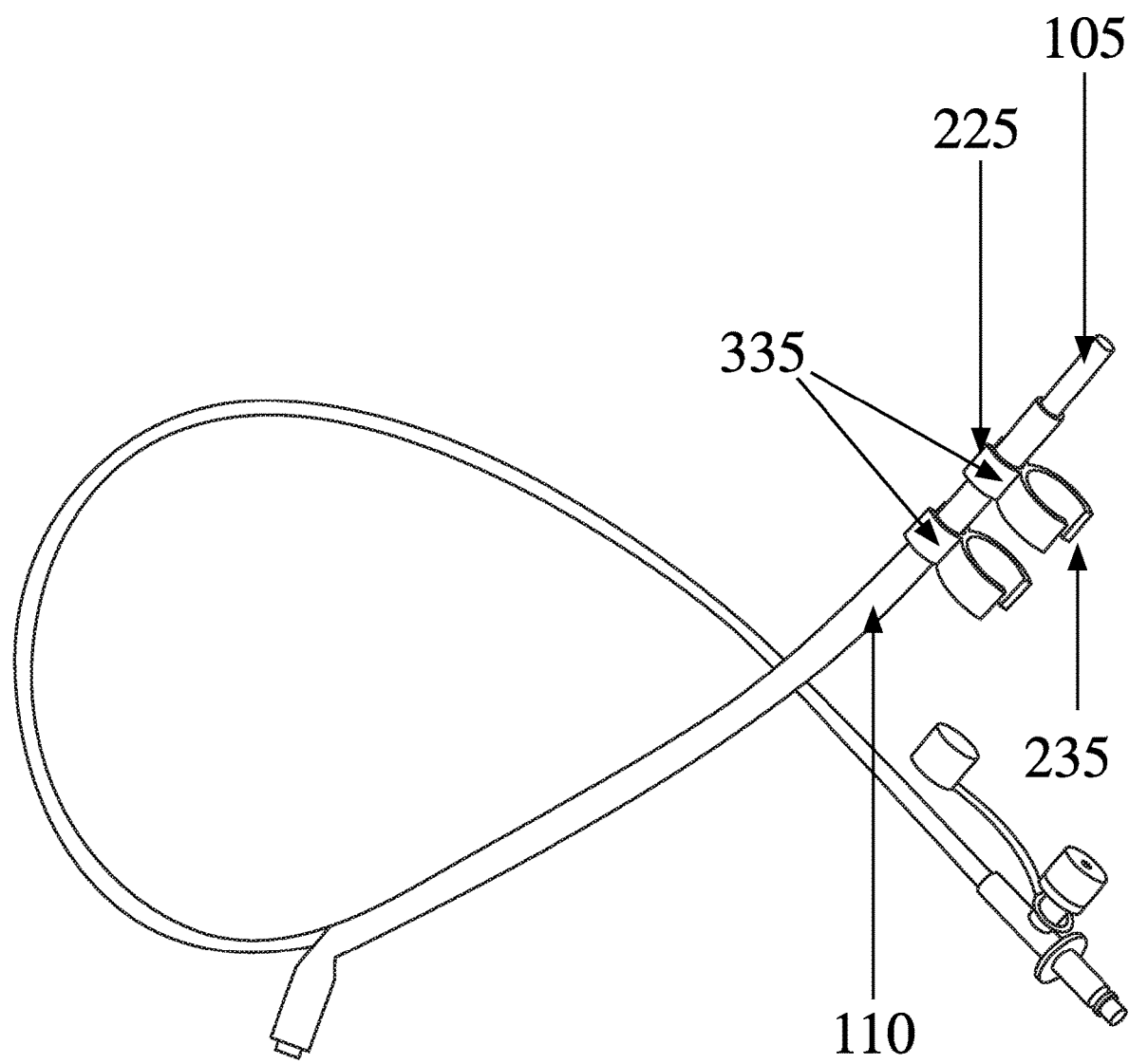
FIG. 2 is a schematic drawing of a manipulator with two finger clips attached to an introducer sheath and a catheter inserted into the sheath, according to various embodiments of the invention.

In an embodiment of the invention, a manipulator is an accessory for single finger guidance and manipulation of the sheath 110 used to insert an IUPC or a Foley catheter. FIG. 2 shows a schematic drawing of two 'in line' manipulators 335 each with a finger clip 235 and each attached via a sheath clip 225 to a sheath 110 and a catheter 105 inserted into the sheath 110, according to various embodiments of the invention. In an embodiment of the invention, the combination of the finger clip 235 and the sheath clip 225 can be referred to as a 'two clip manipulator' 335. In various embodiments of the invention, the attachment of a sheath to a finger via a manipulator enables a medical professional to use one hand to introduce the cather into the sheath and the other (single) hand to correctly orient the sheath in the cervix, to position the catheter correctly in the uterus. In various embodiments of the invention, the attachment of a sheath to a finger, enables a medical professional to use a one handed method to apply the tip of the introducer sheath at the correct angle inside vagina and the cervix around curvature of the fetal presenting part. This is in contrast to the method depicted in FIG. 1 where the rotation and manipulation of the introducer sheath relative to the cervicovaginal junction to the presenting part can require the outer second hand angling the sheath from the outside with the second non vaginal hand.

Figure 7:
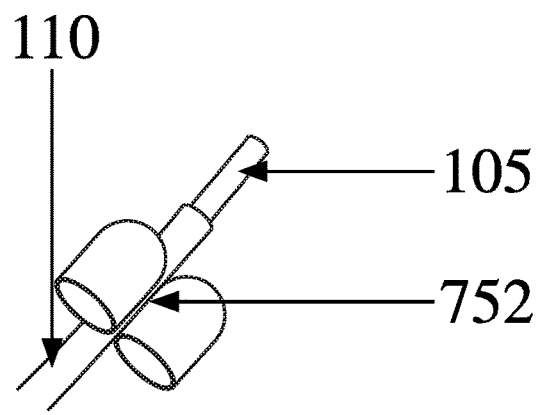
FIG. 7 is a schematic drawing of a manipulator with two thimbles attached to a sheath and a catheter inserted into the sheath, according to various embodiments of the invention.
Figure 8:
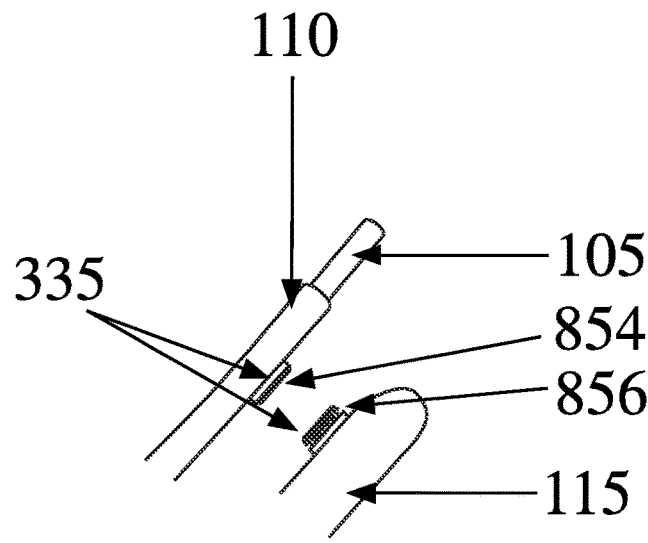
FIG. 8 is a schematic drawing of a manipulator with a Velcro loop patch attached to a sheath and a catheter inserted into the sheath and a Velcro hook patch applied to a finger glove, according to various embodiments of the invention.
Figure 13:
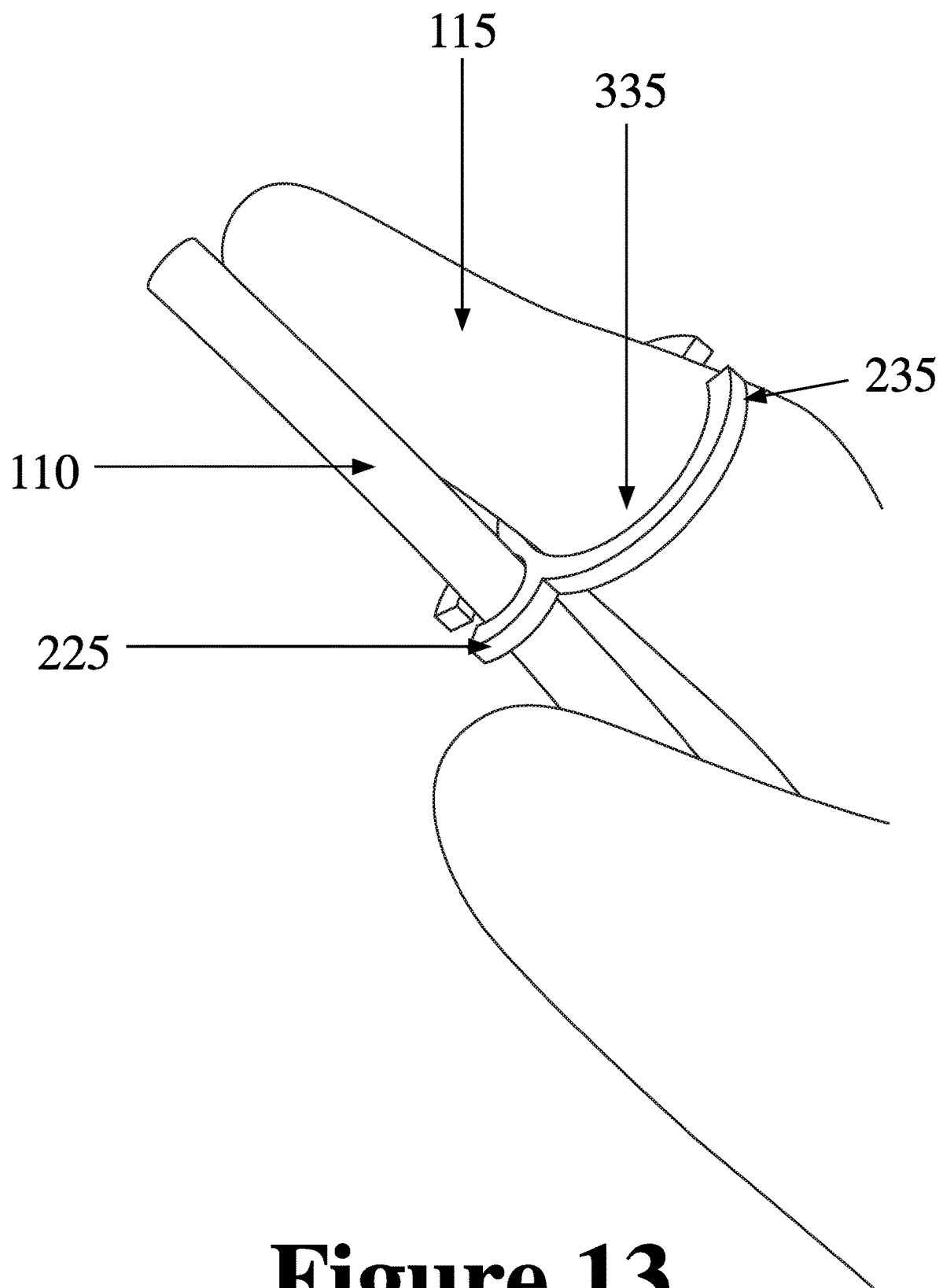
FIG. 13 is a schematic drawing of a two clip manipulator, where the smaller clip can attach the manipulator to the sheath and the larger clip can attach the manipulator to a gloved finger, according to various embodiments of the invention.

In an embodiment of the invention, the manipulator can be adjustably attached to the sheath by using an adjustable clip, an adjustable ring, a fixed ring that can slide over the sheath when pressure is applied perpendicular to the main axis of rotation of the sheath but that can affix to the sheath when pressure is applied at an angle to the main axis of rotation of the sheath. In an alternative embodiment of the invention, the manipulator can be welded to the catheter. FIG. 13 is a schematic drawing of a two clip manipulator 335, where the sheath clip 225 can attach the manipulator 335 to the sheath 110 and the finger clip 235 can attach the manipulator 335 to a gloved finger 115, according to various embodiments of the invention. In another embodiment of the invention, shown in FIG. 5 and FIG. 8, a Velcro manipulator 545, 854 can be welded to the sheath 110 to orient the catheter 105. In FIG. 8, the Velcro pad manipulator 854, is matched to a Velcro hook 856 to detachably engage the manipulator 335. In an alternative embodiment of the invention, a hybrid clip Velcro comprising the sheath clip 225 can attach the manipulator to the sheath 110 and instead of the finger clip 235 a flexible material can attach the manipulator 335 to a gloved finger 115. In various embodiments of the invention, Velcro hook and Velcro loop are present at the two ends of the flexible material respectively, and are used to secure the two ends of the flexible material to the finger. In various embodiments of the invention, shown in FIG. 3-FIG. 10, the manipulator 335, 440, 545, 650, 752, 854, 956, and 1058 is part of and/or attached to the sheath 110 to adjust the catheter 105. In various embodiments of the invention, shown in FIG. 2, FIG. 8, FIG. 9, FIG. 13 and FIG. 14, the sheath clip 225, 854, 954 can via the finger clip 235, 856, 956 attach the manipulator 335, to the sheath 110 to enable a single finger to orient the catheter 105.

Figure 3:
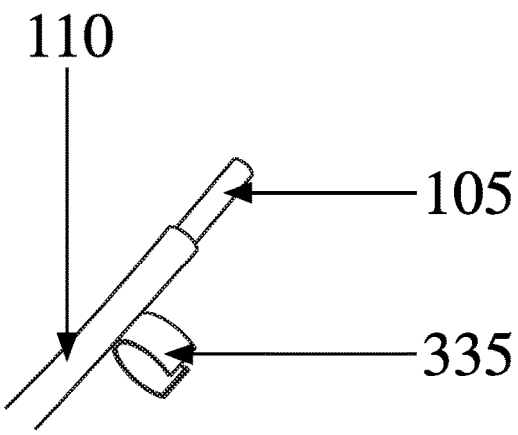
FIG. 3 is a schematic drawing of a manipulator with a single finger clip attached to a sheath and a catheter inserted into the sheath, according to various embodiments of the invention.

In an embodiment of the invention, two fingers can be inserted into the manipulator 335, one finger into each of the finger clips 235, to direct the sheath 110, through the cervix, (i.e., where the finger clips 235 are not 'in line' as shown in FIG. 2). In an embodiment of the invention, a single finger rather than two fingers can be inserted into the manipulator 335 to introduce the sheath through the cervix. FIG. 3 shows a schematic drawing of a manipulator 335 with a single finger clip attached to a sheath 110 and a catheter 105 inserted into the sheath 110, according to various embodiments of the invention.

Figure 4:
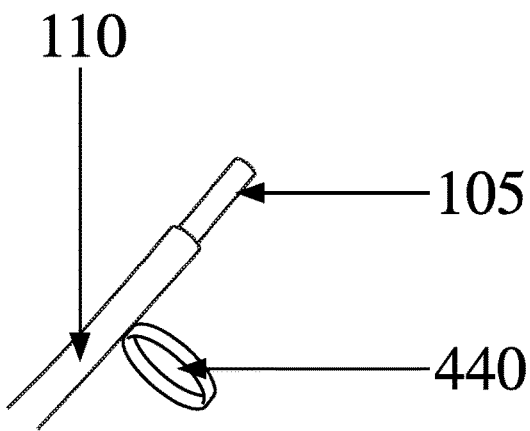
FIG. 4 is a schematic drawing of a manipulator with a single finger ring attached to a sheath and a catheter inserted into the sheath, according to various embodiments of the invention.

The prior art introducer sheath is approximately 25 cm to approximately 56 cm long and is difficult to manipulate with the non vaginal (non introducer) hand. In this range approximately refers to plus or minus ten (10) percent. In various embodiments of the invention, the attachment of a sheath to a finger allows for a shorter introducer sheath. In an embodiment of the invention, the sheath can be between approximately 3 cm and approximately 20 cm in length. In this range approximately refers to plus or minus ten (10) percent. In an embodiment of the invention, a single finger can be flexed and angled internally verses the usual longer sheath version in the prior art that requires two hands to steady and guide/advance towards the cervix. Unexpectedly, by using a one finger design the sheath can be reduced in length and inserted further into the cervix to give the required direction to the catheter. Using a one finger design resulted in an advantageous effect of reducing the length of the sheath and allowing insertion of the sheath further into the cervix to give the required direction to the catheter. In an embodiment of the invention, the catheter is passed through a mini-sheath between approximately 3 cm and approximately 15 cm in length. In an embodiment of the invention, a single finger can be flexed to avoid angling the sheath towards the lateral portion of the cervix. In an unexpected result, angling the sheath away from the lateral portion of the cervix can prevent perforation of the cervix, the amnion 1266 or the chorion 1268 of the amniotic sac or the endometrial lining by the catheter during insertion. The ability to angle the sheath away from the lateral portion of the cervix resulted in an advantageous effect of preventing perforation of the cervix, the amnion 1266 or the chorion 1268 of the amniotic sac or the endometrial lining by the catheter during insertion. Proper placement of the catheter in the intra-amniotic space thus avoiding the extraovular region insures that the amnion 1266 and chorion 1268 of the placenta 1264 remain intact (see FIG. 12). FIG. 4 shows a schematic drawing of a manipulator with a single finger ring 440 attached to a sheath 110 and a catheter 105 inserted into the sheath 110, according to various embodiments of the invention. In an embodiment of the invention, a finger ring instead of a clip has a slim sleek profile on the finger, which protrudes less and is therefore less invasive during a vaginal examination. In various embodiments of the invention, the ring is made of silastic or other flexible plastic which are not so stiff as to be felt.

In various embodiments of the invention, the attachment of a sheath to a single finger enables the catheter to be inserted into a more narrow cervix aperture where the diameter of the cervical canal is less than approximately 2 cm. In an embodiment of the invention, a single finger insinuates through half the conventional cervical dilation, approximately 1 cm to approximately 2 cm instead of approximately 2 cm to approximately 3 cm which allows for earlier insertion of the IUPC (in time in terms of the ripening of the cervix) and therefore longer and more accurate monitoring. In various embodiments of the invention, the IUPC manipulator allows a single finger insertion of the catheter, lowering the cervix dilation aperture requirement from approximately 2 cm to approximately 3 cm to approximately 1 to approximately 2 cm. In this range approximately refers to plus or minus ten (10) percent. This is important as it allows measurement of contractions accurately at an earlier stage. Early measurements are especially important if the mediocal professional is using synthetic oxytocin to induce labor, as the titration of the correct amount of synthetic oxytocin can prevent overdose or more frequent or too strong contractions, making for a safer labor. In addition, more accurate measurement of the timing and duration of the contractions relative to the fetal heart rate can predict fetal hypoxia in cases where decelerations of the fetal heart occur during or following uterine contractions.

In various embodiments of the invention, the manipulator can be a one finger manipulator including a thimble, a ring, a strap, via Velcro to another Velcro pad on the glove, a rubber band. In various embodiments of the invention, the manipulator can be engaged by a single finger of a hand or engaged by a single finger and the thumb for stabilization.

Figure 5:
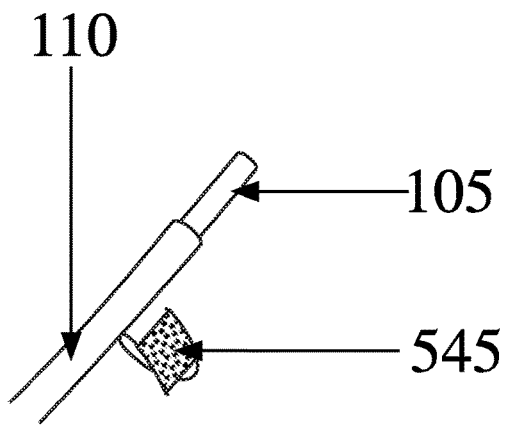
FIG. 5 is a schematic drawing of a manipulator with a single strip of material attached to a sheath and a catheter inserted into the sheath where the single strip of material has a Velcro manipulator pad on each end to fasten the single strip of material around a finger, according to various embodiments of the invention.

FIG. 5 shows a schematic drawing of a manipulator with a single strip of material 545 attached to a sheath 110 and a catheter 105 inserted into the sheath 110 where the single strip of material 545 includes a Velcro pad to fasten the single strip of material to a reciprocal Velcro pad attached to a finger (not shown), according to various embodiments of the invention.

Figure 6:
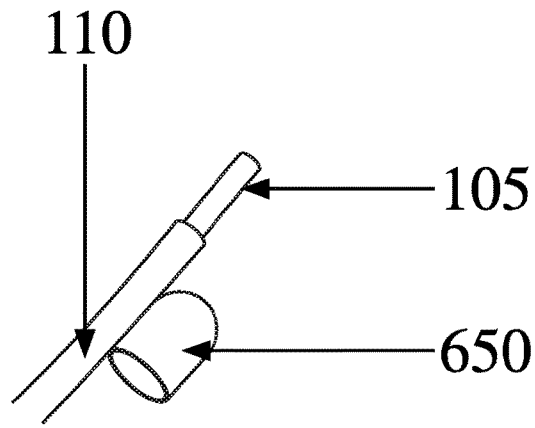
FIG. 6 is a schematic drawing of a manipulator with a single thimble attached to a sheath and a catheter inserted into the sheath, according to various embodiments of the invention.

In an embodiment of the invention, the sheath is stiffer than the catheter. In an embodiment of the invention, the sheath provides a tunnel through which the catheter can be threaded forward into the space between the dilating cervix canal and the fetal presenting part. In various embodiment of the invention, the catheter is thinner and semi-rigid. FIG. 6 shows a schematic drawing of a manipulator with a single thimble 650 attached to a sheath 110 and a catheter 105 inserted into the sheath 110, according to various embodiments of the invention.

In an embodiment of the invention, two fingers can be inserted into the manipulator, one finger into each of the finger clips 752, to direct the sheath 110, through the cervix. FIG. 7 shows a schematic drawing of a manipulator with two thimbles 752 attached to a sheath 110 and a catheter 105 inserted into the sheath 110, according to various embodiments of the invention.

FIG. 8 shows a schematic drawing of a manipulator with a Velcro pad 854 attached to a sheath 110 which can be attached to Velcro loop patch 856. A catheter 105 can be inserted into the sheath 110 and the Velcro hook patch 856 applied to a finger glove can be used to direct a catheter 105 inserted into the sheath 110 into the cervix, according to various embodiments of the invention.

In an embodiment of the invention, the portion 235, 335, 440, 650, 752, 856, 956 of the manipulator 335 that is engaged by the finger is placed on the ventral side of the index finger, with the sheath slightly proximal behind the fingertip. Next the portion of the manipulator 335 that engages the sheath 110 is pressed onto the non-fenestrated side of the sheath 110. Then the medical examiner slides the finger into the cervix and inside the cervix. The manipulator is adapted to allow the sheath 110 to be steered antepartum toward the uterus cavity, where the sheath position enables the catheter 105 to travel parallel to the main axis of the finger with the catheter 105 proximal end at a fingertip position in the center of the dilated opening of the cervix to enter the uterus. Once the sheath 110 is located correctly inside the cervix, the medical examiner then uses his other hand to slide/push the catheter 105 through the sheath to guide the catheter 105 through the cervix, around the presenting part into the uterine cavity. After the catheter 105 is positioned correctly, the medical examiner withdraws the sheath 110 over the catheter outside of the vagina and peels away the sheath 110 leaving the catheter 105 in place.

Figure 9:
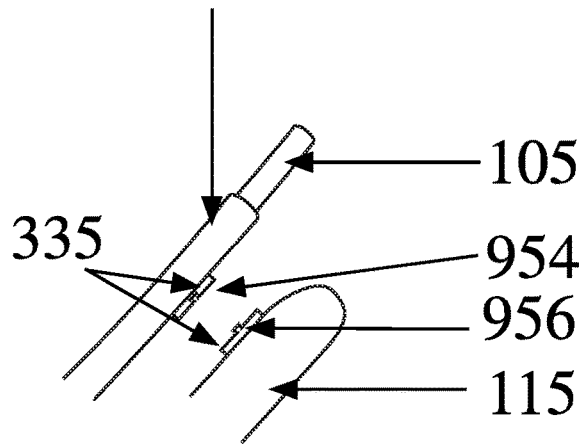
FIG. 9 is a schematic drawing of a manipulator with an indent clip attached to a sheath and a catheter inserted into the sheath and a protruding clip applied to a finger glove, according to various embodiments of the invention.
Figure 14:
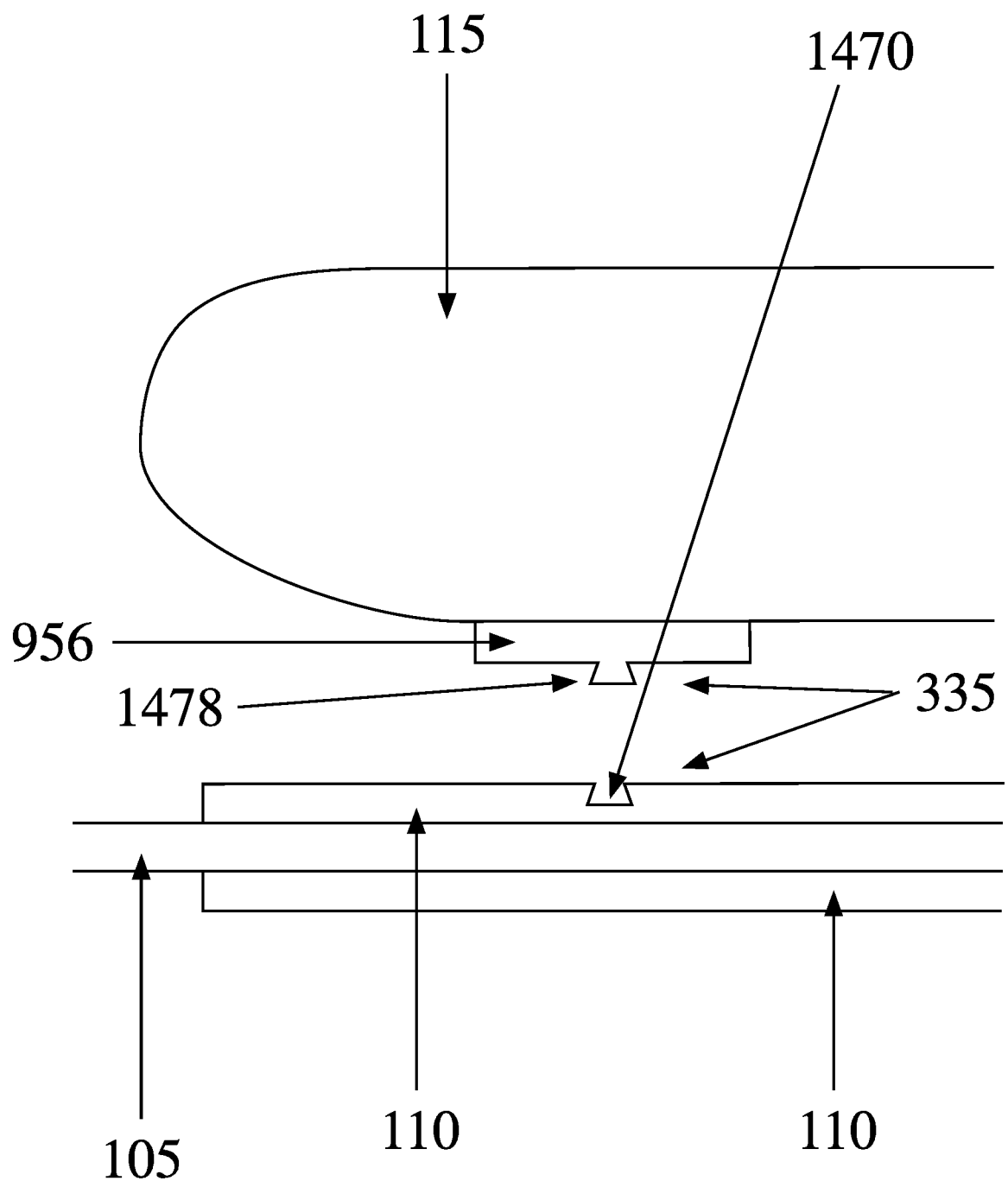
FIG. 14 is a schematic drawing of a sheath with a receptacle opening in the distal dorsal convex aspect opposite the fenestration that can receive a male nipple snap applied to a finger glove via a protrusion from a ring or clip, according to various embodiments of the invention.

FIG. 9 shows a schematic drawing of a manipulator 335 with an indent sheath clip 954 attached to a sheath 110 and a catheter 105 inserted into the sheath 110 and a protrusion from the finger clip 956 applied to a finger glove 115, where the protrusion inserts into the indent, according to various embodiments of the invention. FIG. 14 shows a schematic drawing of a sheath 110 with a catheter 105 inserted in the sheath 110 and an indent or a receptacle opening 1470 in the sheath 110 that is adapted to receive a protrusion or a male nipple snap 1478 extending from the finger clip 956 applied or attached to a finger glove 115 via a ring or finger clip 956, according to various embodiments of the invention. In an embodiment of the invention, the sheath can be fenestrated and the recepticle opening 1470 can be a distal dorsal convex aspect opposite the fenestration (not shown) that can receive the male nipple snap 956 applied or attached to the finger glove 115.

Figure 10:
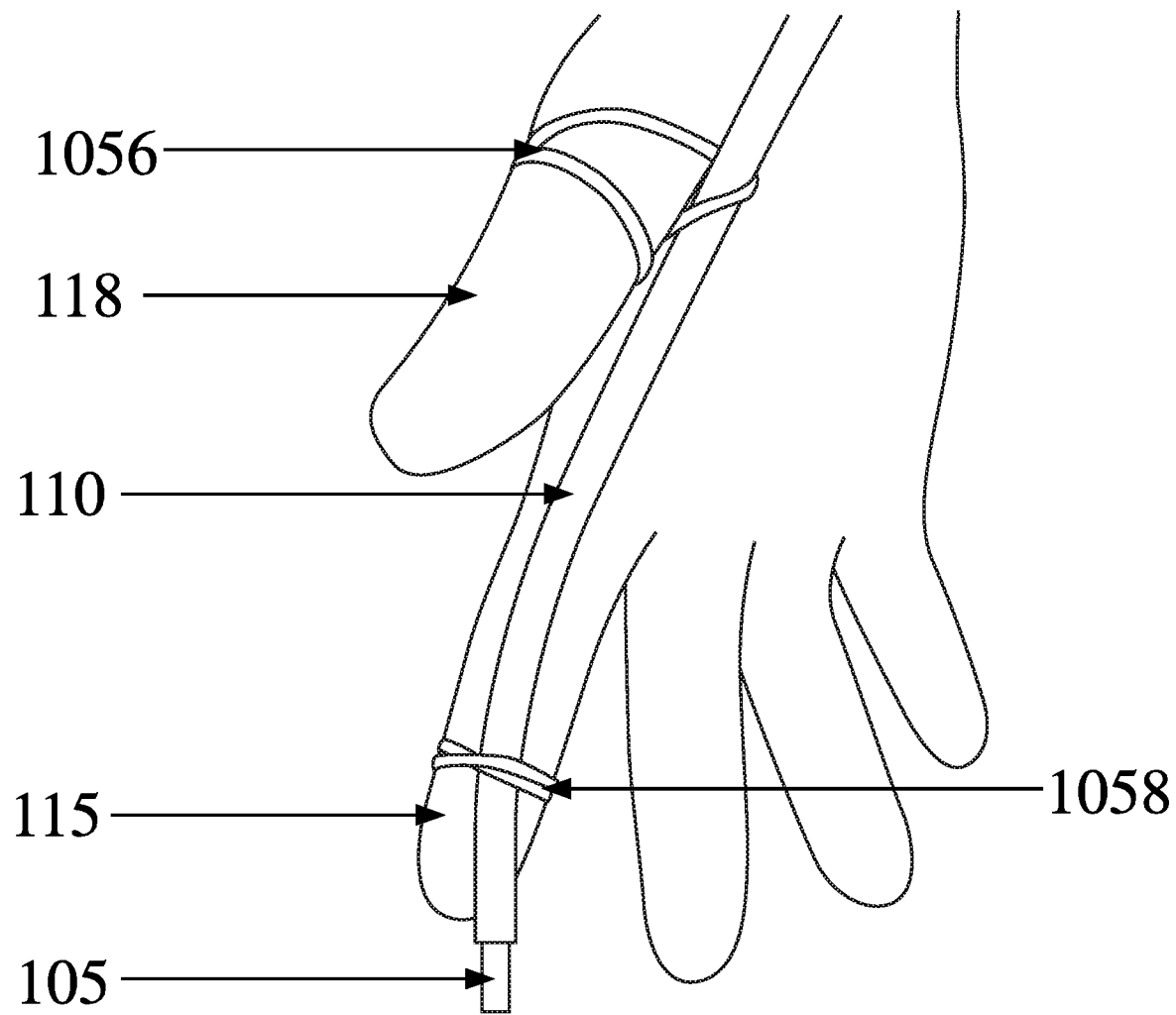
FIG. 10 is a schematic drawing of a gloved hand with the sheath attached to the thumb and index finger of a gloved hand and the catheter inserted into the sheath, according to various embodiments of the invention.

FIG. 10 shows a schematic drawing of a gloved hand with the sheath 110 attached through two points of attachment 1056, 1058 to the thumb glove 118 and glove index finger 115 of a gloved hand and the catheter 105 inserted into the sheath 110, according to various embodiments of the invention. In an embodiment of the invention, the thumb and finger connections through two points of attachment 1056, 1058 can be either as a clip or a band 1056, 1058. In an embodiment of the invention, if the sheath 110 was attached only to the opposite side of the fenestration it can serve as an IUPC without the need for a tab to remove the catheter 105 from the sheath 110. The sheath 110 can be slid over the catheter 105 until the sheath 110 was outside the vagina, then peeled off.

Figure 11:
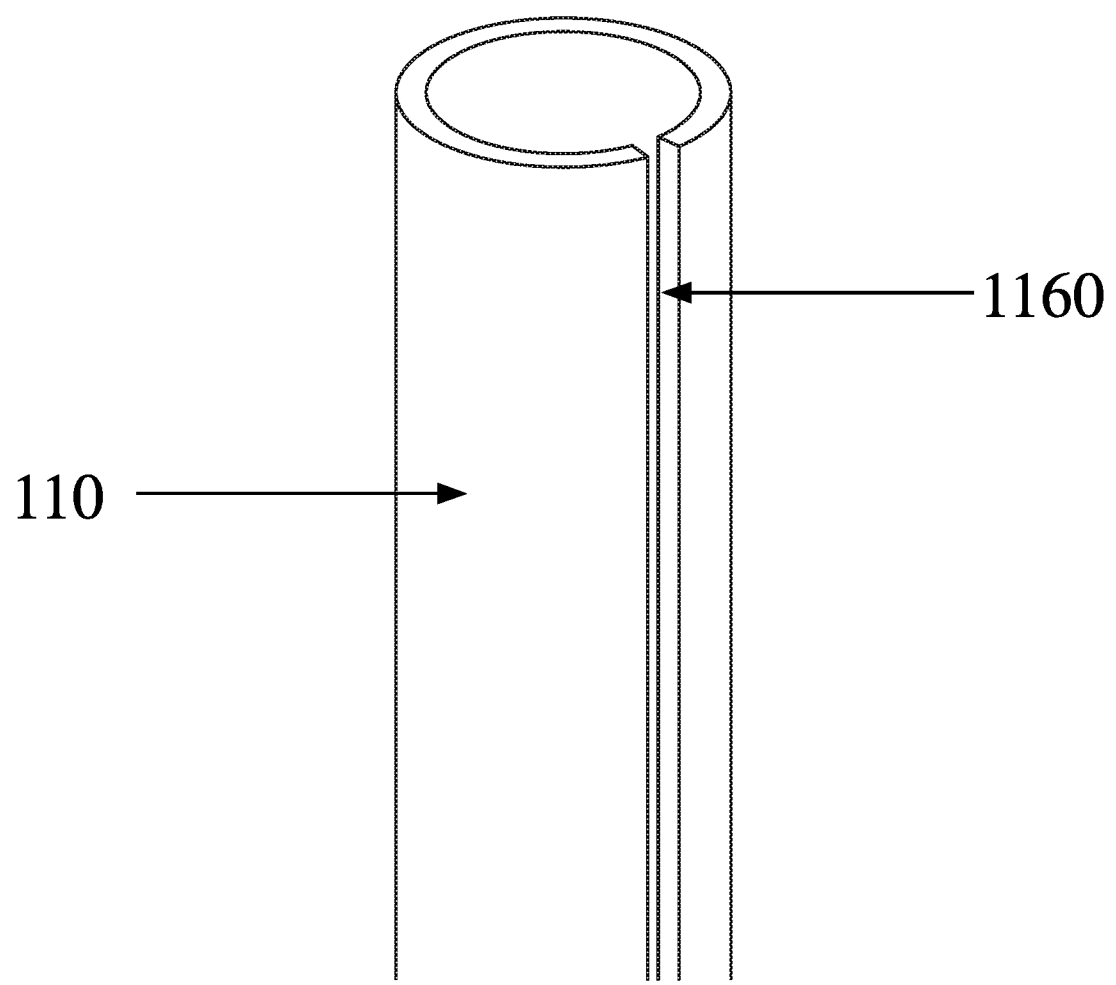
FIG. 11 is a schematic drawing of a sheath with an opening to allow easy removal of the sheath from the catheter, according to various embodiments of the invention.

FIG. 11 is a schematic drawing of a fenestrated sheath 110 with an opening 1160 to allow easy removal of the sheath 110 from the catheter (not shown), according to various embodiments of the invention. In an embodiment of the invention, a clip that attaches to the manipulator has a fenestration gap just like fenestrated sheath opening 1160. In an embodiment of the invention, a clip can function as a sheath tab to peel off the sheath 110 from the catheter. In an embodiment of the invention, a sheath is shorter between approximately 16 cm and approximately 20 cm can be fenestrated. In an embodiment of the invention, a sheath between approximately 6 cm and approximately 16 cm, can be fenestrated. In this range approximately refers to plus or minus ten (10) percent. In an embodiment of the invention, the sheath needs a fenestration on the concave side of the sheath so that the sheath can be peeled off the catheter, or in other words, the catheter can remain in place after insertion and the sheath simply peeled away from the catheter through the fenestration.

FIG. 14 is a schematic drawing of a sheath 110 with a receptacle opening 1470 in the distal dorsal convex aspect opposite the fenestration (not shown) that can receive a male nipple snap 1478 applied to a finger glove 115 via a protrusion from a ring or clip 956, according to various embodiments of the invention.

In various embodiments of the invention, catheter placement is critical to patient outcome. The medical professional is insinuating a catheter in a specific location during a dynamic process of cervical dilation during labor. The space constraints and physical constraints including the human hand examining dilatation of the cervix, the amount of dilation, the degree of cervical elasticity (including the consistency as firm or soft, due to pro staglandins creating protease activity breaking down collagen and elastin in the cervix stroma to allow it to stretch), the degree of effacement (change of the tubular cervix to a flat pancake shape), the station of the fetal presenting part relative to pelvic landmarks (e.g., the descent from the true pelvis into the outlet and vagina, through soft tissue). The aperture of the cervix as it dilates and effaces is the channel for the catheter. Currently, it is not possible to manually place a catheter during a digital pelvic examination (i.e., with fingers) through a cervix that is under approximately 2 cm to approximately 3 cm dilated (depending on the medical examiner's gender, and the physical size of the diameter and volume of the medical examiner's distal fingers doing the insertion/manipulation). A one finger design reduces this limitation nearly in half.

In an embodiment of the present invention, the manipulator 335, the sheath 110 and/or the catheter 105 are made of a signal-opaque material. In an embodiment of the present invention, the manipulator 335, the sheath 110 and/or the catheter 105 are made of a radio-opaque material. Fluoroscopy can be used to visualize the location of manipulator 335, the sheath 110 and/or the catheter 105 by the radio-opaque material and therefore to assist in placing the catheter in the correct location. In another embodiment of the present invention, the proximal end of the catheter that is inserted into the cervix can be ball-tipped with a radio-opaque ball, or structured for expanding the duct to allow the catheter and the introduces and sheath to enter the cervix. The catheter can include a marking device located adjacent to the proximal tip, such as a radio-opaque mark, to assist in guiding the catheter to a desired location in the womb, as viewed fluoroscopically. Additionally, a retractable sheath with a radio-opaque mark can be provided to allow the sheath and introducer to be removed while the catheter remains in place. According to another aspect of the invention, the proximal end of the catheter includes an expansion mechanism for expanding the cervix. The method includes the further step of expanding a section of the cervix with the expansion mechanism before passing the catheter into the womb. This can be especially useful in the case where the cervix has not ripened and has a very narrow stricture.

In an embodiment of the invention, the introducer sheath would not exceed the length of the medical examiner hand and not protrude from the vagina. If the manipulator clip is also fenestrated or exists on the opposite surface, the clip itself can manipulated and relocated from the distal end to the proximal end of the sheath, and following catheter insertion, can serve as an adjustable pull tab to strip the stiffer introducer sheath from the catheter. Being adjustable and detachable, relocation of the clip along the introducer sheath is feasible.

In an embodiment of the present invention, a Radio Frequency IDentification (RFID) tag is embedded in one or more of the manipulator embodiments 335, the sheath 110 and the catheter 105. The chain of custody and/or compatibility of one or more of the manipulator embodiments 335, the sheath 110 and the catheter 105 can therefore be determined. In an embodiment of the present invention, a CCD camera is embedded in one or more of the manipulator embodiments 335, the sheath 110 and the catheter 105. The approximate position of the one or more of the manipulator embodiments 335, the sheath 110 and the catheter 105 can then be detected through a combination of RFID location and camera detection. In an embodiment of the invention, one or more of the manipulator embodiments 335, the sheath 110 and the catheter 105 are automatically dispensed by an apparatus that recognizes the RFID tags in the one or more of the manipulator 335, the sheath 110 and the catheter 105. In an embodiment of the invention, the RFID tag is used to identify the characteristics (fenestration, diameter, angle and edge nature) of the one or more of the manipulator embodiments 335, the sheath 110 and the catheter 105 being supplied. In one embodiment of the invention, the RFID tag operates using an Ultra High Frequency (UHF) signal. In another embodiment of the invention, the RFID tag operates using a microwave frequency signal.

In one embodiment the RFID tag is read only. In another embodiment, the RFID tag contains an Electrically Erasable Programmable Read-Only Memory (EPROM), which enables both read and write functions. In an embodiment of the invention, the RFID tag is passive. In another embodiment of the invention, the RFID tag is semi passive containing a source of energy such as a battery to allow the tag to be constantly powered. In a further embodiment of the invention, the RFID tag is active, containing an internal power source, such as a battery, which is used to power any Integrated Circuits (ICs) in the tag and generate the outgoing signal. In another embodiment, the tag has the ability to enable location sensing through a photo sensor.

In one embodiment of the invention, means of communication with a base station is embedded in one or more of the manipulator 335, the sheath 110 and the catheter 105.

In one embodiment of the invention, the communication means utilizes one or more of a wireless local area network; a wireless wide area network; a cellular network; a satellite network; a Wi-Fi network; and a pager network. In one embodiment of the invention, a modem capable of communicating with one or more of the aforementioned networks is embedded in one or more of the manipulator 335, the sheath 110 and the catheter 105. In the following discussion the term 'cellular modem' will be used to describe the device embedded. The term 'cellular modem' will be herein used to identify any device of comparable size capable of communicating over one or more of the aforementioned networks. In one embodiment of the invention, the cellular modem can be a Code Division Multiple Access (CDMA) modem. In an embodiment of the invention, a RFID reader and associate integrated circuit processor can be embedded together with the cellular modem in one or more of the manipulator 335, the sheath 110 and the catheter 105. In such an embodiment, the RFID tags and RFID reader can be positioned to optimize the RFID read of the RFID tags.

In an embodiment of the invention, the RFID reader and associate processor can be in communication with the cellular modem. In an embodiment of the invention, the cellular modem is in communication with a base station and can transmit one or more parameters selected from the group consisting of one or more RFID tag location, one or more RFID tag identification code, canal type, patient, diagnosis and time stamp.

In one embodiment of the invention the RFID code uses the IEEE format and is Electronic Product Code (EPC) readable. In another embodiment of the invention the RFID code uses the UCC format and is Universal Product Code (UPC) readable. In another embodiment, the format is compatible for EPC, European Article Number (EAN) and UPC read and write functions.

In an embodiment of the invention, the device method or system can be used for the treatment of humans. In an embodiment of the invention, the device method or system can be used for the treatment of animals. In an embodiment of the invention, the device method or system can be used in veterinary applications. In an embodiment of the invention, the device method or system can be used in medical applications.

In an embodiment of the invention, a method of positioning a catheter through a cervix into a uterus comprising the steps of receiving a fenestrated sheath with a proximal end and a distal end, receiving a single finger manipulator with a clip to attach to the fenestrated sheath and means to position the fenestrated sheath, attaching the single finger manipulator to the fenestrated sheath, inserting the proximal end into the cervix, positioning the proximal end in the cervix with the single finger manipulator and inserting the catheter through the distal end of the fenestrated sheath into the uterus.

In an embodiment of the invention, a method of positioning a catheter through a cervix into a uterus comprising the steps of receiving a fenestrated sheath with a proximal end and a distal end, receiving a single finger manipulator with a clip to attach to the fenestrated sheath and means to position the fenestrated sheath, attaching the single finger manipulator to the fenestrated sheath, inserting the proximal end into the cervix, positioning the proximal end in the cervix with the single finger manipulator and inserting the catheter through the distal end of the fenestrated sheath into the uterus, further comprising withdrawing the fenestrated sheath from the vagina while the catheter remains in the uterus.

In an embodiment of the invention, a method of positioning a catheter through a cervix into a uterus comprising the steps of receiving a fenestrated sheath with a proximal end and a distal end, receiving a single finger manipulator with a clip to attach to the fenestrated sheath and means to position the fenestrated sheath, attaching the single finger manipulator to the fenestrated sheath, inserting the proximal end into the cervix, positioning the proximal end in the cervix with the single finger manipulator and inserting the catheter through the distal end of the fenestrated sheath into the uterus, further comprising removing the fenestrated sheath from the catheter while the catheter remains in the uterus.

In an embodiment of the invention, a method of positioning a catheter through a cervix into a uterus comprising the steps of receiving a fenestrated sheath with a proximal end and a distal end, receiving a single finger manipulator with a clip to attach to the fenestrated sheath and means to position the fenestrated sheath, attaching the single finger manipulator to the fenestrated sheath, inserting the proximal end into the cervix, positioning the proximal end in the cervix with the single finger manipulator and inserting the catheter through the distal end of the fenestrated sheath into the uterus, further comprising removing the fenestrated sheath from the catheter while the catheter remains in the uterus, where the fenestrated sheath is used to remove the catheter from the fenestrated sheath.

In an embodiment of the invention, a method of positioning a catheter through a cervix into a uterus comprising the steps of receiving a fenestrated sheath with a proximal end and a distal end, receiving a single finger manipulator with a clip to attach to the fenestrated sheath and means to position the fenestrated sheath, attaching the single finger manipulator to the fenestrated sheath, inserting the proximal end into the cervix, positioning the proximal end in the cervix with the single finger manipulator and inserting the catheter through the distal end of the fenestrated sheath into the uterus, where the single finger manipulator is attached to a single finger of a glove.

In an embodiment of the invention, a method of positioning a catheter through a cervix into a uterus comprising the steps of receiving a fenestrated sheath with a proximal end and a distal end, receiving a single finger manipulator with a clip to attach to the fenestrated sheath and means to position the fenestrated sheath, attaching the single finger manipulator to the fenestrated sheath, inserting the proximal end into the cervix, positioning the proximal end in the cervix with the single finger manipulator and inserting the catheter through the distal end of the fenestrated sheath into the uterus, where the single finger manipulator is detachable from a single finger of a glove.

In an embodiment of the invention, a method of positioning a catheter through a cervix into a uterus comprising the steps of receiving a fenestrated sheath with a proximal end and a distal end, receiving a single finger manipulator with a clip to attach to the fenestrated sheath and means to position the fenestrated sheath, attaching the single finger manipulator to the fenestrated sheath, inserting the proximal end into the cervix, positioning the proximal end in the cervix with the single finger manipulator and inserting the catheter through the distal end of the fenestrated sheath into the uterus, where the single finger manipulator includes a Velcro hook and a Velcro loop to attach to a single finger of a glove.

In an embodiment of the invention, a method of positioning a catheter through a cervix into a uterus comprising the steps of receiving a fenestrated sheath with a proximal end and a distal end, receiving a single finger manipulator with a clip to attach to the fenestrated sheath and means to position the fenestrated sheath, attaching the single finger manipulator to the fenestrated sheath, inserting the proximal end into the cervix, positioning the proximal end in the cervix with the single finger manipulator and inserting the catheter through the distal end of the fenestrated sheath into the uterus, where the single finger manipulator includes a Velcro hook and a Velcro loop to attach to a single finger of a glove, where the Velcro hook is associated with the single finger manipulator and the Velcro loop is attached to the fenestrated sheath.

In an embodiment of the invention, a method of positioning a catheter through a cervix into a uterus comprising the steps of receiving a fenestrated sheath with a proximal end and a distal end, receiving a single finger manipulator with a clip to attach to the fenestrated sheath and means to position the fenestrated sheath, attaching the single finger manipulator to the fenestrated sheath, inserting the proximal end into the cervix, positioning the proximal end in the cervix with the single finger manipulator and inserting the catheter through the distal end of the fenestrated sheath into the uterus, where the single finger manipulator is detachable from the fenestrated sheath.

In an embodiment of the invention, a method of positioning a catheter through a cervix into a uterus comprising the steps of receiving a fenestrated sheath with a proximal end and a distal end, receiving a single finger manipulator with a clip to attach to the fenestrated sheath and means to position the fenestrated sheath, attaching the single finger manipulator to the fenestrated sheath, inserting the proximal end into the cervix, positioning the proximal end in the cervix with the single finger manipulator and inserting the catheter through the distal end of the fenestrated sheath into the uterus, where the single finger manipulator is attached to the fenestrated sheath using a clip.

In an embodiment of the invention, a method of positioning a catheter through a cervix into a uterus comprising the steps of receiving a fenestrated sheath with a proximal end and a distal end, receiving a single finger manipulator with a clip to attach to the fenestrated sheath and means to position the fenestrated sheath, attaching the single finger manipulator to the fenestrated sheath, inserting the proximal end into the cervix, positioning the proximal end in the cervix with the single finger manipulator and inserting the catheter through the distal end of the fenestrated sheath into the uterus, where the catheter can slide through the fenestrated sheath to allow the fenestrated sheath to be inserted into the cervix and position the catheter for advancement in the uterus.

In an embodiment of the invention, a method of positioning a catheter through a cervix into a uterus comprising the steps of receiving a fenestrated sheath with a proximal end and a distal end, receiving a single finger manipulator with a clip to attach to the fenestrated sheath and means to position the fenestrated sheath, attaching the single finger manipulator to the fenestrated sheath, inserting the proximal end into the cervix, positioning the proximal end in the cervix with the single finger manipulator and inserting the catheter through the distal end of the fenestrated sheath into the uterus, where the catheter can slide through the fenestrated sheath to allow the fenestrated sheath to be inserted into the cervix and position the catheter for advancement in the uterus, where the fenestrated sheath can slide along the catheter to allow the fenestrated sheath to be withdrawn from the vagina while the catheter remains in position.

In an embodiment of the invention, a method of positioning a catheter through a cervix into a uterus comprising the steps of receiving a fenestrated sheath with a proximal end and a distal end, receiving a single finger manipulator with a clip to attach to the fenestrated sheath and means to position the fenestrated sheath, attaching the single finger manipulator to the fenestrated sheath, inserting the proximal end into the cervix, positioning the proximal end in the cervix with the single finger manipulator and inserting the catheter through the distal end of the fenestrated sheath into the uterus, further comprising means to visualize one or more of position of the single finger introducer, position of the fenestrated sheath, position of the catheter, and position of the fenestrated sheath relative to position of the catheter in the uterus.

In an embodiment of the invention, a method of positioning a catheter through a cervix into a uterus comprising the steps of receiving a fenestrated sheath with a proximal end and a distal end, receiving a single finger manipulator with a clip to attach to the fenestrated sheath and means to position the fenestrated sheath, attaching the single finger manipulator to the fenestrated sheath, inserting the proximal end into the cervix, positioning the proximal end in the cervix with the single finger manipulator and inserting the catheter through the distal end of the fenestrated sheath into the uterus, where the single finger manipulator can slide along the fenestrated sheath to allow the fenestrated sheath to be one or both located in the cervix and withdrawn from the cervix while the catheter remains in position.

In an embodiment of the invention, a method of positioning a catheter in a uterus comprising the steps of receiving a fenestrated sheath with a proximal end and a distal end and a single finger manipulator attached to the fenestrated sheath towards the proximal end, using a single gloved finger to engage the single finger manipulator to position the proximal end of the fenestrated sheath in a cervix, using the single finger manipulator to locate the proximal end of the fenestrated sheath in one of the upper cervical region and the lower uterine segment adjacent to a fetal presenting part, positioning the catheter through the distal end of the fenestrated sheath in the uterus and withdrawing the fenestrated sheath with the single finger manipulator from the cervix.

In an embodiment of the invention, a method of positioning a catheter in a uterus comprising the steps of receiving a fenestrated sheath with a proximal end and a distal end and a single finger manipulator attached to the fenestrated sheath towards the proximal end, using a single gloved finger to engage the single finger manipulator to position the proximal end of the fenestrated sheath in a cervix, using the single finger manipulator to locate the proximal end of the fenestrated sheath in one of the upper cervical region and the lower uterine segment adjacent to a fetal presenting part, positioning the catheter through the distal end of the fenestrated sheath in the uterus and withdrawing the fenestrated sheath with the single finger manipulator from the cervix, where the catheter can slide inside the fenestrated sheath to allow the fenestrated sheath to be withdrawn from the cervix while the catheter to remain in position.

In an embodiment of the invention, a method of positioning a catheter in a uterus comprising the steps of receiving a fenestrated sheath with a proximal end and a distal end and a single finger manipulator attached to the fenestrated sheath towards the proximal end, using a single gloved finger to engage the single finger manipulator to position the proximal end of the fenestrated sheath in a cervix, using the single finger manipulator to locate the proximal end of the fenestrated sheath in one of the upper cervical region and the lower uterine segment adjacent to a fetal presenting part, positioning the catheter through the distal end of the fenestrated sheath in the uterus and withdrawing the fenestrated sheath with the single finger manipulator from the cervix, further comprising means to one or more of visualize insertion of the fenestrated sheath, introduction of the catheter, location of the catheter and withdrawal of the fenestrated sheath from the cervix.

In an embodiment of the invention, a method of positioning a catheter in a uterus comprising the steps of receiving a fenestrated sheath with a proximal end and a distal end and a single finger manipulator attached to the fenestrated sheath towards the proximal end, using a single gloved finger to engage the single finger manipulator to position the proximal end of the fenestrated sheath in a cervix, using the single finger manipulator to locate the proximal end of the fenestrated sheath in one of the upper cervical region and the lower uterine segment adjacent to a fetal presenting part, positioning the catheter through the distal end of the fenestrated sheath in the uterus and withdrawing the fenestrated sheath with the single finger manipulator from the cervix, where the single finger manipulator is adapted to release and adjust along a length of the fenestrated sheath.

In an embodiment of the invention, a method of positioning a catheter in a uterus comprising the steps of receiving a fenestrated sheath with a proximal end and a distal end and a single finger manipulator attached to the fenestrated sheath towards the proximal end, using a single gloved finger to engage the single finger manipulator to position the proximal end of the fenestrated sheath in a cervix, using the single finger manipulator to locate the proximal end of the fenestrated sheath in one of the upper cervical region and the lower uterine segment adjacent to a fetal presenting part, positioning the catheter through the distal end of the fenestrated sheath in the uterus and withdrawing the fenestrated sheath with the single finger manipulator from the cervix, where the single finger manipulator is adapted to release and adjust along a length of the fenestrated sheath, where the single finger manipulator is adapted to engage the fenestrated sheath to allow the fenestrated sheath to be withdrawn from the cervix while the catheter remains in position.

In an embodiment of the invention, a method of positioning a catheter in a uterus comprising the steps of receiving a fenestrated sheath with a proximal end and a distal end and a single finger manipulator attached to the fenestrated sheath towards the proximal end, using a single gloved finger to engage the single finger manipulator to position the proximal end of the fenestrated sheath in a cervix, using the single finger manipulator to locate the proximal end of the fenestrated sheath in one of the upper cervical region and the lower uterine segment adjacent to a fetal presenting part, positioning the catheter through the distal end of the fenestrated sheath in the uterus and withdrawing the fenestrated sheath with the single finger manipulator from the cervix, where the single finger manipulator is detachably affixed to the fenestrated sheath.

In an embodiment of the invention, a method of positioning a catheter in a uterus comprising the steps of receiving a fenestrated sheath with a proximal end and a distal end and a single finger manipulator attached to the fenestrated sheath towards the proximal end, using a single gloved finger to engage the single finger manipulator to position the proximal end of the fenestrated sheath in a cervix, using the single finger manipulator to locate the proximal end of the fenestrated sheath in one of the upper cervical region and the lower uterine segment adjacent to a fetal presenting part, positioning the catheter through the distal end of the fenestrated sheath in the uterus and withdrawing the fenestrated sheath with the single finger manipulator from the cervix, where the single finger manipulator is affixed to the fenestrated sheath prior to insertion in the cervix.

In an embodiment of the invention, a method of positioning a catheter in a uterus comprising the steps of receiving a fenestrated sheath with a proximal end, a distal end and a manipulator, where the manipulator is attached to the fenestrated sheath, where the manipulator is adapted to be fixably attached to and detached from the fenestrated sheath, using the manipulator to insert the proximal end of the fenestrated sheath into a cervix, using the manipulator to locate the proximal end of the catheter in the cervix, inserting the catheter through the distal end of the sheath around a fetal presenting part into the uterus and locating the catheter in position.

In an embodiment of the invention, a method of positioning a catheter in a uterus comprising the steps of receiving a fenestrated sheath with a proximal end, a distal end and a manipulator, where the manipulator is attached to the fenestrated sheath, where the manipulator is adapted to be fixably attached to and detached from the fenestrated sheath, using the manipulator to insert the proximal end of the fenestrated sheath into a cervix, using the manipulator to locate the proximal end of the catheter in the cervix, inserting the catheter through the distal end of the sheath around a fetal presenting part into the uterus and locating the catheter in position, where the catheter can slide inside the fenestrated sheath to allow the fenestrated sheath to be withdrawn from the cervix while the catheter remains in the position.

In an embodiment of the invention, a method of positioning a catheter in a uterus comprising the steps of receiving a fenestrated sheath with a proximal end, a distal end and a manipulator, where the manipulator is attached to the fenestrated sheath, where the manipulator is adapted to be fixably attached to and detached from the fenestrated sheath, using the manipulator to insert the proximal end of the fenestrated sheath into a cervix, using the manipulator to locate the proximal end of the catheter in the cervix, inserting the catheter through the distal end of the sheath around a fetal presenting part into the uterus and locating the catheter in position, further comprising means to one or more of visualize insertion of the fenestrated sheath, introduction of the catheter, location of the catheter and withdrawal of the fenestrated sheath from the cervix.

In an embodiment of the invention, a method of positioning a catheter in a uterus comprising the steps of receiving a fenestrated sheath with a proximal end, a distal end and a manipulator, where the manipulator is attached to the fenestrated sheath, where the manipulator is adapted to be fixably attached to and detached from the fenestrated sheath, using the manipulator to insert the proximal end of the fenestrated sheath into a cervix, using the manipulator to locate the proximal end of the catheter in the cervix, inserting the catheter through the distal end of the sheath around a fetal presenting part into the uterus and locating the catheter in position, where the manipulator is adapted to release and adjust along a length of the fenestrated sheath.

In an embodiment of the invention, a method of positioning a catheter in a uterus comprising the steps of receiving a fenestrated sheath with a proximal end, a distal end and a manipulator, where the manipulator is attached to the fenestrated sheath, where the manipulator is adapted to be fixably attached to and detached from the fenestrated sheath, using the manipulator to insert the proximal end of the fenestrated sheath into a cervix, using the manipulator to locate the proximal end of the catheter in the cervix, inserting the catheter through the distal end of the sheath around a fetal presenting part into the uterus and locating the catheter in position, where the manipulator is adapted to release and adjust along a length of the fenestrated sheath, where the manipulator is adapted to engage the fenestrated sheath to allow the sheath to be withdrawn from the cervix while the catheter remains in position.

In an embodiment of the invention, a method of positioning a catheter in a uterus comprising the steps of receiving a fenestrated sheath with a proximal end, a distal end and a manipulator, where the manipulator is attached to the fenestrated sheath, where the manipulator is adapted to be fixably attached to and detached from the fenestrated sheath, using the manipulator to insert the proximal end of the fenestrated sheath into a cervix, using the manipulator to locate the proximal end of the catheter in the cervix, inserting the catheter through the distal end of the sheath around a fetal presenting part into the uterus and locating the catheter in position, where the single finger manipulator is detachably affixed to the fenestrated sheath.

In an embodiment of the invention, a device for positioning a catheter antepartum through a uterus into a uterus comprises a fenestrated sheath with a proximal end and a distal end, where the fenestrated sheath is sized to allow a catheter to be introduced into a cervix, where the catheter is inserted antepartum through the cervix, where the catheter is positioned inside the uterus and a manipulator, where the manipulator is adapted to be adjustably attached to and detached from the fenestrated sheath, where the manipulator is adapted to position the fenestrated sheath toward the uterine cavity and be positioned adjacent to a fetal presenting part.

In an embodiment of the invention, a device for positioning a catheter antepartum through a uterus into a uterus comprises a fenestrated sheath with a proximal end and a distal end, where the fenestrated sheath is sized to allow a catheter to be introduced into a cervix, where the catheter is inserted antepartum through the cervix, where the catheter is positioned inside the uterus and a manipulator, where the manipulator is adapted to be adjustably attached to and detached from the fenestrated sheath, where the manipulator is adapted to position the fenestrated sheath toward the uterine cavity and be positioned adjacent to a fetal presenting part, where the manipulator allows attachment of a single finger to the fenestrated sheath at a distance from the distal end of between a lower limit of approximately 1 mm and an upper limit of approximately 3 cm.

In an embodiment of the invention, a device for positioning a catheter antepartum through a uterus into a uterus comprises a fenestrated sheath with a proximal end and a distal end, where the fenestrated sheath is sized to allow a catheter to be introduced into a cervix, where the catheter is inserted antepartum through the cervix, where the catheter is positioned inside the uterus and a manipulator, where the manipulator is adapted to be adjustably attached to and detached from the fenestrated sheath, where the manipulator is adapted to position the fenestrated sheath toward the uterine cavity and be positioned adjacent to a fetal presenting part, where the manipulator allows attachment of a distal aspect of the fenestrated sheath to two fingers.

In an embodiment of the invention, a device for positioning a catheter antepartum through a uterus into a uterus comprises a fenestrated sheath with a proximal end and a distal end, where the fenestrated sheath is sized to allow a catheter to be introduced into a cervix, where the catheter is inserted antepartum through the cervix, where the catheter is positioned inside the uterus and a manipulator, where the manipulator is adapted to be adjustably attached to and detached from the fenestrated sheath, where the manipulator is adapted to position the fenestrated sheath toward the uterine cavity and be positioned adjacent to a fetal presenting part, where the manipulator is permanently attached to the fenestrated sheath.

In an embodiment of the invention, a device for positioning a catheter antepartum through a uterus into a uterus comprises a fenestrated sheath with a proximal end and a distal end, where the fenestrated sheath is sized to allow a catheter to be introduced into a cervix, where the catheter is inserted antepartum through the cervix, where the catheter is positioned inside the uterus and a manipulator, where the manipulator is adapted to be adjustably attached to and detached from the fenestrated sheath, where the manipulator is adapted to position the fenestrated sheath toward the uterine cavity and be positioned adjacent to a fetal presenting part, where the manipulator is detachable from a distal aspect of the fenestrated sheath.

In an embodiment of the invention, a device for positioning a catheter antepartum through a cervix into a uterus comprises a fenestrated sheath with a proximal end and a distal end, where the fenestrated sheath is hollow and sized to allow a catheter to be inserted through fenestrated sheath and thereby through the cervix and positioned inside the uterus, where the distal end allows the fenestrated sheath to be removed from the catheter outside the cervix and a manipulator with a clip to allow the manipulator to be fixably attached to and detached from the fenestrated sheath, where the manipulator is adapted to allow the fenestrated sheath to be inserted into the cervix, where the manipulator is adapted to allow the catheter to be positioned inside the uterus.

In an embodiment of the invention, a device for positioning a catheter antepartum through a cervix into a uterus comprises a fenestrated sheath with a proximal end and a distal end, where the fenestrated sheath is hollow and sized to allow a catheter to be inserted through fenestrated sheath and thereby through the cervix and positioned inside the uterus, where the distal end allows the fenestrated sheath to be removed from the catheter outside the cervix and a manipulator with a clip to allow the manipulator to be fixably attached to and detached from the fenestrated sheath, where the manipulator is adapted to allow the fenestrated sheath to be inserted into the cervix, where the manipulator is adapted to allow the catheter to be positioned inside the uterus, where the clip is fenestrated and allows for one or both placement of the clip onto the fenestrated sheath and lateral traction away from the fenestrated sheath.

In an embodiment of the invention, a kit for positioning a catheter antepartum through a cervix into a uterus cavity comprises a fenestrated sheath with a proximal end and a distal end, one or more manipulators, where the one or more manipulators are adapted to be fixably attached to and detached from the fenestrated sheath, where the one or more manipulators are adapted to allow the fenestrated sheath to pass through the cervix and be steered toward the uterus cavity, where each of the one or more manipulators are sized to allow different size fingers to direct the position of the fenestrated sheath and a catheter sized to pass through the fenestrated sheath and thereby through the cervix and be positioned inside the uterus cavity.

In an embodiment of the invention, a kit for positioning a catheter antepartum through a cervix into a uterus cavity comprises a sheath with a proximal end and a distal end, a manipulator with a fenestrated clip, where the fenestrated clip allows the manipulator to be fixably attached to and detached from the sheath, where the manipulator is contoured to allow the sheath to be steered antepartum toward the uterus cavity and a catheter sized to pass through the sheath with the fenestrated clip attached and thereby through the cervix and be positioned inside the uterus cavity.

In an embodiment of the invention, a finger manipulator to manipulate a catheter through a cervix into a uterus cavity comprises a fenestrated clip adapted to be fixably attached to and detached from a sheath, where the sheath is hollow and fenestrated, where the sheath is adapted to fit the catheter through the sheath, a clasp adapted to be steered by a single finger and a bridge to connect the fenestrated clip to the clasp, where the finger manipulator is adapted to allow the sheath to be steered antepartum toward the uterus cavity, where the sheath position enables the catheter to travel parallel to the main axis of the finger with a proximal end of the catheter at a fingertip position in the center of the dilated opening of the cervix.

In an embodiment of the invention, a method comprises receiving a sheath with a proximal end and a distal end, receiving a manipulator including a clip adapted to attach the manipulator to the distal end, wherein the manipulator is adapted to allow a single finger to be inserted into the manipulator to position the proximal end, attaching the manipulator to the distal end, inserting the proximal end into a cervix of a uterus, inserting a single finger into the manipulator to position the proximal end in the cervix, and inserting a catheter through the distal end of the sheath through the cervix into the uterus to position the catheter in the uterus.

In an embodiment of the invention, a method comprises receiving a sheath including a proximal end, a distal end and a manipulator adapted to allow one of two fingers and two fingers of a glove to be connected to the manipulator, where the manipulator is positioned at the distal end, inserting the proximal end into a cervix of a uterus, inserting one of two fingers and a glove into the manipulator to position the proximal end, and inserting a catheter through the distal end of the sheath through the cervix into the uterus to position the catheter in the uterus.

In an embodiment of the invention, a method comprises receiving a fenestrated sheath including a proximal end, a distal end and a manipulator, where the manipulator is attached to the fenestrated sheath, where the manipulator is adapted to be fixably attached to and detached from the fenestrated sheath, using the manipulator to insert the proximal end of the fenestrated sheath into a cervix of a uterus, inserting a catheter through the distal end of the fenestrated sheath in a position around a fetal presenting part into the uterus, and locating the catheter the position.

In an embodiment of the invention, a method comprises receiving a sheath with a proximal end and a distal end and a manipulator attached to the sheath towards the proximal end, using a single gloved finger to engage the manipulator to position the proximal end of the sheath in a cervix, using the manipulator to locate the proximal end of the sheath in one of the upper cervical region and the lower uterine segment adjacent to a fetal presenting part, and inserting a catheter through the distal end of the sheath in one of the upper cervical region and the lower uterine segment.

In an embodiment of the invention, a method comprises receiving a sheath including a proximal end, a distal end and a manipulator adapted to allow one of a finger and a finger glove to be connected to the manipulator, where the manipulator is positioned at the distal end, inserting the proximal end into a cervix of a uterus, inserting one of a finger and a gloved finger into the manipulator to position the proximal end, inserting a catheter through the distal end of the sheath through the cervix into the uterus to position the catheter in the uterus, and one or both steering and guiding the angle of trajectory of the sheath in a patient in labor.

In an embodiment of the invention, a method comprises receiving a sheath including a proximal end, a distal end and a manipulator adapted to allow one of a finger and a gloved finger to be connected to the manipulator, where the manipulator is positioned at the proximal end, inserting the proximal end into a cervix of a uterus, associating one or both the finger and the gloved finger with the manipulator, inserting through the distal end a catheter which exits at the proximal end into one or both the cervix and the uterus, and positioning the catheter in the cervix and uterus by adjusting one or both the catheter and the position of the proximal end with the manipulator.

The foregoing description of embodiments of the methods, systems, and components of the present invention has been provided for the purposes of illustration and description. It is not intended to be exhaustive or to limit the invention to the precise forms disclosed. Many modifications and variations will be apparent to one of ordinary skill in the relevant arts. For example, steps performed in the embodiments of the invention disclosed can be performed in alternate orders, certain steps can be omitted, and additional steps can be added. The embodiments were chosen and described in order to best explain the principles of the invention and its practical application, thereby enabling others skilled in the art to understand the invention for various embodiments and with various modifications that are suited to the particular used contemplated. Other embodiments are possible and are covered by the invention. Such embodiments will be apparent to persons skilled in the relevant art(s) based on the teachings contained herein. The breadth and scope of the present invention should not be limited by any of the above-described exemplary embodiments, but should be defined only in accordance with the following claims and their equivalents.

What is claimed is:

1. A method for introducing and positioning a catheter into a uterine amniotic cavity comprising:
   a) attaching a two clip manipulator comprising a first clip, a second clip, and an arc through the first clip to a single finger of a user, where the two clip manipulator has a first main axis of rotation parallel with an axis of the single finger which passes through a phalange and a knuckle, where the first clip comprises a first arm, a second arm and a first fenestration, where the first arm comprises a first width, a first thickness, a first length and a first curvature, where the second arm comprises the first width, the first thickness, the first length and the first curvature, where the first clip is adapted to surround the single finger while leaving a first gap in which the single finger is not completely surrounded by the first clip, where the first gap corresponds to the first fenestration, where the second clip comprises a third arm, a fourth arm and a second fenestration, where the third arm comprises the first width, the first thickness, a second length and a second curvature, where the fourth arm comprises the first width, the first thickness, the second length and the second curvature, where the first length is greater than the second length, where the second curvature is greater than the first curvature, where a positive direction is perpendicular to the first main axis of rotation and toward the second fenestration, where lateral traction away from a sheath is in an opposite direction perpendicular to the first main axis of rotation and toward the first fenestration, where the second clip is adapted to surround the sheath while leaving a second gap in which the sheath is not completely surrounded by the second clip, where the second gap corresponds to the second fenestration, where the sheath comprises a distal end, a proximal end, a third length and a second main axis of rotation, where the second main axis of rotation passes through the proximal end and the distal end, where the first clip and the second clip are joined at the arc, where the first fenestration is located opposite the arc, where the second fenestration is located opposite the arc, where the two clip manipulator is adapted to release laterally from the single finger;
   b) inserting a catheter into the sheath, where the second clip is adapted to attach to the sheath such that the second main axis of rotation is parallel with the first main axis of rotation, where the two clip manipulator is adapted to detach and re-attach to the sheath laterally through the second clip at a plurality of locations along the third length from the distal end to the proximal end;
   c) associating the two clip manipulator with the sheath laterally through the second fenestration of the second clip, where the first clip is adapted such that a first force exerted by the single finger through the first clip in a first direction co-linear with the first main axis of rotation is transferred directly to the sheath through the second clip and moves the sheath in the first direction, where the first clip is adapted such that a second force exerted by the single finger through the first clip in the positive direction is transferred directly to the sheath through the second clip and moves the sheath in the positive direction, and where the first clip is adapted to release and adjust from the sheath such that the lateral traction away from the sheath exerted by the single finger through the first clip in the opposite direction releases the two clip manipulator laterally from the sheath;

d) inserting, with the single finger associated with the two clip manipulator, the sheath through a cervix towards the uterine cavity;

e) advancing the catheter into the uterus; and f) positioning the catheter in the uterus by adjusting one or both a first position of the sheath in the cervix and a second position of the two clip manipulator.

2. The method of claim 1, where the two clip manipulator is adapted to be attached to a finger glove.

3. The method of claim 2, where the two clip manipulator is detachable from the finger glove.

4. The method of claim 1, further comprising a second two clip manipulator adapted to detachably attach to the single finger and the sheath.

5. A method for introducing, positioning and removing a catheter from a uterine amniotic cavity comprising:

a) attaching a two clip manipulator comprising a first clip, a second clip, and an arc through the first clip to a single finger of a user, where the two clip manipulator has a first main axis of rotation parallel with an axis of the single finger which passes through a phalange and a knuckle, where the first clip comprises a first arm, a second arm and a first fenestration, where the first arm comprises a first width, a first thickness, a first length and a first curvature, where the second arm comprises the first width, the first thickness, the first length and the first curvature, where the first clip is adapted to surround the single finger while leaving a first gap in which the single finger is not completely surrounded by the first clip, where the first gap corresponds to the first fenestration, where the second clip comprises a third arm, a fourth arm and a second fenestration, where the third arm comprises the first width, the first thickness, a second length and a second curvature, where the fourth arm comprises the first width, the first thickness, the second length and the second curvature, where the first length is greater than the second length, where the second curvature is greater than the first curvature, where a positive direction is perpendicular to the first main axis of rotation and toward the second fenestration, where lateral traction away from a sheath is in an opposite direction perpendicular to the first main axis of rotation and toward the first fenestration, where the second clip is adapted to surround the sheath while leaving a second gap in which the sheath is not completely surrounded by the second clip, where the second gap corresponds to the second fenestration, where the sheath comprises a distal end, a proximal end, a third length and a second main axis of rotation, where the second main axis of rotation passes through the proximal end and the distal end, where the first clip and the second clip are joined at the arc, where the first fenestration is located opposite the arc, where the second fenestration is located opposite the arc, where the two clip manipulator is adapted to release laterally from the single finger;

b) inserting a catheter into the sheath, where the second clip is adapted to attach to the sheath such that the second main axis of rotation is parallel with the first main axis of rotation, where the two clip manipulator is adapted to detach and re-attach to the sheath laterally through the second clip at a plurality of locations along the third length from the distal end to the proximal end;

c) associating the two clip manipulator with the sheath laterally through the second fenestration of the second clip, where the first clip is adapted such that a first force exerted by the single finger through the first clip in a first direction co-linear with the first main axis of rotation is transferred directly to the sheath through the second clip and moves the sheath in the first direction, where the sheath further comprises a third fenestration;

d) inserting, with the single finger associated with the two clip manipulator, the sheath through a cervix towards the uterine cavity;

e) advancing the catheter into the uterus; and f) positioning the catheter in the uterus by adjusting one or both a first position of the sheath in the cervix and a second position of the two clip manipulator, where the first clip is adapted such that a second force exerted by the single finger through the first clip in the positive direction is transferred directly to the sheath through the second clip and moves the sheath in the positive direction, and where the first clip is adapted such that when the third fenestration is aligned with the second fenestration, the lateral traction away from the sheath exerted by the single finger through the first clip in the opposite direction releases the two clip manipulator attached to the sheath from the catheter.

6. The method of claim 5, where when the third fenestration is not aligned with the second fenestration, then the two clip manipulator can be detached from the sheath to allow the sheath to be further inserted into the cervix and the two clip manipulator can be re-attached to the sheath to position the catheter for continued advancement in the uterus.

7. The method of claim 5, where the sheath can slide along the catheter to allow the sheath to be withdrawn from the vagina while the catheter remains in position.

8. The method of claim 7, further comprising removing the sheath from the vagina while the catheter remains in the uterus, where when the third fenestration is aligned with the second fenestration, then the two clip manipulator and the sheath are used to peel the sheath from around the catheter to remove the sheath from the catheter while the catheter remains in the uterus.

9. The method of claim 5, where the second force attaches the second clip to the sheath.

10. A method for attaching a two clip manipulator to a catheter to direct the catheter to monitor uterine contractions comprising:

a) receiving a two clip manipulator comprising a first clip and a second clip, where the first clip comprises a first pair of arms having a first width, a first thickness, a first length forming the first pair of arms and a first fenestration and having a first main axis of rotation, where the first main axis of rotation is parallel with an axis of a single extended finger of a user, where the second clip comprises a second pair of arms having the first width, the first thickness and a second length forming the second pair of arms and a second fenestration, where the first length is greater than the second length, where the two clip manipulator is adapted to attach onto the single finger of the user through the first clip, where the first pair of arms and the first fenestration are adapted to allow the first clip to surround the single finger while leaving a first gap in which the single finger is not completely surrounded by the first clip, where the first gap corresponds to the first fenestration, where the first clip and the second clip are contiguous, where the second clip is adapted to release laterally from a fenestrated sheath and adjust and re-attach longitudinally to the fenestrated sheath;

b) attaching the two clip manipulator to the single finger laterally through the first fenestration of the first clip;

c) attaching the two clip manipulator to the fenestrated sheath laterally through the second fenestration of the second clip, where the second clip surrounds the fenestrated sheath while leaving a second gap in which the fenestrated sheath is not completely surrounded by the second clip, where the second gap corresponds to the second fenestration, where the first fenestration of the first clip is adapted such that a first force exerted by the single finger through the first clip in a first direction co-linear with the first main axis of rotation is transferred directly to the fenestrated sheath through the second clip and moves the fenestrated sheath in the first direction, where the first fenestration of the first clip is adapted such that a second force exerted by the single finger through the first clip in a direction perpendicular to the first main axis of rotation is transferred directly to the fenestrated sheath through the second clip and moves the fenestrated sheath in the second direction;

d) inserting the fenestrated sheath, the two clip manipulator and the single finger inside a cervix;

e) positioning a catheter in a uterus by adjusting one or both a position of the fenestrated sheath and a position of the two clip manipulator with the single finger; and f) inserting the catheter through the fenestrated sheath into the uterus.

11. The method of claim 10, where the single finger is inserted in a glove to engage the two clip manipulator.

12. The method of claim 10, further comprising a second two clip manipulator adapted to detachably attach to the single finger and the fenestrated sheath.

13. The method of claim 12, where one or both the two clip manipulator and the second two clip manipulator are adapted to be attached to a finger glove.

14. The method of claim 13, where one or both the two clip manipulator and the second two clip manipulator are adapted to detach from the finger glove.

* * * * *